(12) United States Patent
Beshore et al.

(10) Patent No.: US 8,883,850 B2
(45) Date of Patent: Nov. 11, 2014

(54) NAPHTHALENE CARBOXAMIDE M1 RECEPTOR POSITIVE ALLOSTERIC MODULATORS

(75) Inventors: Douglas C. Beshore, Lower Gwynedd, PA (US); Christina Ng DiMarco, Conshohocken, PA (US); Scott D. Kukuk, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 7 days.

(21) Appl. No.: 13/698,288

(22) PCT Filed: May 23, 2011

(86) PCT No.: PCT/US2011/037493
§ 371 (c)(1),
(2), (4) Date: Nov. 16, 2012

(87) PCT Pub. No.: WO2011/149801
PCT Pub. Date: Dec. 1, 2011

(65) Prior Publication Data
US 2013/0059860 A1    Mar. 7, 2013

Related U.S. Application Data

(60) Provisional application No. 61/349,348, filed on May 28, 2010.

(51) Int. Cl.
*A61K 31/19* (2006.01)
*A01N 37/10* (2006.01)
*A61K 31/16* (2006.01)
*A61K 31/192* (2006.01)

(52) U.S. Cl.
CPC .............. *A61K 31/16* (2013.01); *A61K 31/192* (2013.01)
USPC ........... 514/569; 514/336; 514/341; 514/346; 514/357; 514/406; 546/275.4; 546/275.7; 546/282.1; 546/333

(58) Field of Classification Search
CPC ...................................... A61K 31/16
USPC ............ 514/254.05, 336, 341, 346, 357, 406, 514/569; 546/275.4, 275.7, 282.1, 333
See application file for complete search history.

(56) References Cited

U.S. PATENT DOCUMENTS

| | | | |
|---|---|---|---|
| 4,840,951 A | 6/1989 | Iwaskaki et al. | |
| 5,281,720 A | 1/1994 | Young et al. | |
| 8,258,135 B2 * | 9/2012 | Chang et al. | 514/249 |
| 8,273,737 B2 * | 9/2012 | Kuduk et al. | 514/218 |
| 8,426,598 B2 * | 4/2013 | Kuduk et al. | 546/159 |
| 8,436,016 B2 * | 5/2013 | Kuduk et al. | 514/312 |
| 2004/0044061 A1 | 3/2004 | Gerlach et al. | |
| 2004/0147570 A1 | 7/2004 | Gerlach et al. | |
| 2009/0227625 A1 | 9/2009 | Hachtel et al. | |
| 2012/0184518 A1 * | 7/2012 | Schilling et al. | 514/171 |

FOREIGN PATENT DOCUMENTS

| | | |
|---|---|---|
| EP | 0283924 | 9/1998 |
| WO | 2004/073639 | 9/2004 |
| WO | WO2010/047990 | 4/2010 |

OTHER PUBLICATIONS

R. M. Eglen et al., "Therapeutic Opportunities from Muscarinic Receptor Research", 2001, pp. 409-414, vol. 22, No. 8, Trends in Pharmacological Sciences.
A. Fisher, Therapeutc Strategies in Azheimer's Disease: M1 Muscarnic Agoniss, 2000, pp. 101-112, vol. 84, Jpn. J. Pharmacol.
T. A. Spalding et al, "Discovery of an Ectopic Activation Site on the M1 Muscarinic Receptor", 2002, pp. 1297-1302, Molecular Pharmacology.
S. Lazareno et al., "Analogs of WIN 62.577 Define a Second Allosteric Site on Muscarinic Receptors", 2002, pp. 1492-1505, vol. 62, Molecular Pharmacology.
S. Lazareno et al., "Allosteric Interactions of Staurosporine and Other Indolocarbazoles with N-[methyl-3-H] Scopolamine and Acetylcholine at Muscarinic Receptor Subtypes: Identification of a Second Allosteric Site",2000, pp. 194-207, vol. 58, Molecular Pharmacology.

* cited by examiner

*Primary Examiner* — My-Chau T Tran
(74) *Attorney, Agent, or Firm* — Sylvia A. Ayler; John C. Todaro

(57) ABSTRACT

The present invention is directed to naphthalene carboxamide compounds of formula (I) which are M1 receptor positive allosteric modulators and that are useful in the treatment of diseases in which the M1 receptor is involved, such as Alzheimers disease, schizophrenia, pain or sleep disorders. The invention is also directed to pharmaceutical compositions comprising the compounds and to the use of the compounds and compositions in the treatment of diseases mediated by the M1 receptor.

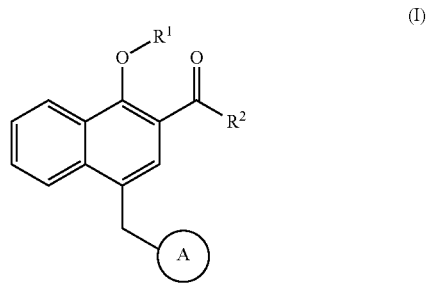

18 Claims, No Drawings

NAPHTHALENE CARBOXAMIDE M1 RECEPTOR POSITIVE ALLOSTERIC MODULATORS

CROSS REFERENCE TO RELATED APPLICATIONS

This application is the National Stage of International Application No. PCT/US2011/037493 filed on May 23, 2011, which claims the benefit under 35 U.S.C. 119(e) of U.S. Provisional Application No. 61/349,348, filed May 28, 2010.

FIELD OF THE INVENTION

The invention is directed to a class of naphthalene carboxamide compounds, their salts, pharmaceutical compositions comprising them and their use in therapy of the human body. In particular, the invention is directed to a class of naphthalene carboxamide compounds, which are muscarinic M1 receptor positive allosteric modulators, and hence are useful in the treatment of Alzheimer's disease and other diseases mediated by the muscarinic M1 receptor.

BACKGROUND OF THE INVENTION

Alzheimer's disease is a common neurodegenerative disease affecting the elderly, resulting in progressive memory impairment, loss of language and visual-spatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid β peptide (Aβ). Aβ is a 39-43 amino acid produced in the brain by processing of the beta-amyloid precursor protein (APP) by the beta-amyloid protein cleaving enzyme ("beta secretase" or "BACE") and gamma-secretase. The processing leads to accumulation of Aβ in the brain.

Cholinergic neurotransmission involves the binding of acetylcholine either to the nicotinic acetylcholine receptor (nAChR) or to the muscarinic acetylcholine receptor (mAChR). It has been hypothesized that cholinergic hypofunction contributes to the cognitive deficits of patients suffering from Alzheimer's disease. Consequently, acetyl cholinesterase inhibitors, which inhibit acetylcholine hydrolysis, have been approved in the United States for use in the treatment of the cognitive impairments of Alzheimer's disease patients. While acetyl cholinesterase inhibitors have provided some cognitive enhancement in Alzheimer's disease patients, the therapy has not been shown to change the underlying disease pathology.

A second potential pharmacotherapeutic target to counteract cholinergic hypofunction is the activation of muscarinic receptors. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions. The muscarinic M1 receptor, which is prevalent in the cerebral cortex, hippocampus and striatum, has been found to have a major role in cognitive processing and is believed to have a role in the pathophysiology of Alzheimer's Disease. See, Eglen et al., TRENDS in Pharmacological Sciences, 2001, 22:8, 409-414. In addition, unlike acetyl cholinesterase inhibitors, which are known to provide only symptomatic treatment, M1 agonists also have the potential to treat the underlying disease mechanism of Alzheimer's disease. The cholinergic hypothesis of Alzheimer's disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective αAPPs fragment, thereby preventing the formation of the Aβ peptide. Thus, M1 agonists may alter APP processing and enhance αAPPs secretion. See, Fisher, Jpn. J. Pharmacol., 2000, 84:101-112. However, M1 ligands which have been developed and studied for Alzheimer's disease have produced side effects common to other muscarinic receptor ligands, such as sweating, nausea and diarrhea. See, Spalding et al., Mol. Pharmacol, 2002, 61:6, 1297-1302.

The muscarinic receptors are known to contain one or more allosteric sites, which may alter the affinity with which muscarinic ligands bind to the primary binding or orthosteric sites. See, for example, S. Lazareno et al., Mol. Pharmacol., 2002, 62:6, 1491-1505; S. Lazareno et al., Mol. Pharmacol., 2000, 58, 194-207.

Thus, the compounds of the invention, which are muscarinic M1 receptor positive allosteric modulators, are believed to be useful in the treatment of Alzheimer's disease and other diseases mediated by the muscarinic M1 receptor.

SUMMARY OF THE INVENTION

The present invention is directed to naphthalene carboxamide compounds that are useful as M1 receptor positive allosteric modulators (PAMs) to treat diseases or disorders in which the M1 receptor is involved. This invention also provides pharmaceutical compositions comprising a PAM, either alone or in combination with one or more therapeutically active compounds and a pharmaceutically acceptable carrier.

The invention is further directed to methods of treating a patient (preferably a human) for diseases or disorders in which the M1 receptor is involved, such as Alzheimer's disease, cognitive impairment, schizophrenia, pain disorders and sleep disorders, by administering to the patient a therapeutically effective amount of a compound of the invention, or a pharmaceutically acceptable salt thereof.

DETAILED DESCRIPTION OF THE INVENTION

In one embodiment, the invention is directed to naphthalene carboxamide compounds of general formula (I),

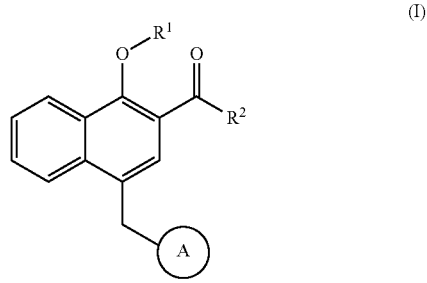

and pharmaceutically acceptable salts thereof, wherein
$R^1$ is selected from the group consisting of
(1) hydrogen,
(2) —$R^3$,
(3) —$C_{1-6}$ alkyl,
(4) —$C_{2-6}$ alkenyl, and
(5) —C(O)N($R^4$)$_2$,
  wherein each is optionally substituted with one or more $R^a$;

$R^2$ is selected from the group consisting of
  (1) hydroxyl, and
  (2) —$N(R^4)_2$,
  wherein each is optionally substituted with one or more $R^a$;
$R^3$ and $R^4$ are independently selected from the group consisting of
  (1) hydrogen,
  (2) hydroxyl,
  (3) —$C_{1-6}$ alkyl,
  (4) —$C_{3-10}$ cycloalkyl, and
  (5) —$C_{5-10}$ heterocyclyl,
  wherein each is optionally substituted with one or more $R^a$;
A is selected from the group consisting of
  (1) —$C_{6-10}$ aryl, and
  (2) —$C_{6-10}$ heteroaryl,
  wherein each is optionally substituted with one or more $R^a$;
$R^a$ is selected from the group consisting of
  (1) hydrogen,
  (2) hydroxyl,
  (3) halogen,
  (4) —O,
  (5) —$C_{1-6}$ alkyl,
  (6) —$C_{3-10}$ cycloalkyl, which is unsubstituted or substituted with one or more hydroxyl,
  (7) —$C_{5-10}$ heteroaryl, which is unsubstituted or substituted with one or more hydroxyl,
  (8) —CN,
  (9) —$OR_3$,
  (10) —$SR_3$,
  (11) —$N(R_4)_n$, and
  (12) —$C(O)R_3O(C)O$; and
n is independently 1 to 4.

In one embodiment, for compounds of formula (I), $R^1$ is selected from the group consisting of
  (1) hydrogen,
  (2) methyl,
  (3) ethyl,
  (4) ethylenyl, and
  (5) $C(O)NHCH_2CH_3$.

In another embodiment, for compounds of formula (I), $R^1$ is hydrogen. In still another embodiment, compounds of formula (I), $R^1$ is methyl.

In one embodiment, for compounds of formula (I), $R^2$ is $N(R^4)_2$ and each $R^4$ is independently selected from the group consisting of
  (1) hydrogen,
  (2) —$C_{3-10}$ cycloalkyl, and
  (3) —$C_{5-10}$ heterocyclyl,
wherein said cycloalkyl and said heterocyclyl are optionally substituted with one or more $R^a$.

In another embodiment of formula (I), $R^2$ is hydroxyl or $N(R^4)_2$, wherein $R^4$ is hydrogen and —$C_{3-10}$ cycloalkyl, which is optionally substituted with one or more $R^a$. In still another embodiment, where $R^2$ is $N(R^4)_2$, $R^4$ is hydrogen and cyclohexyl, which is optionally substituted with one or more $R^a$. In still another embodiment of formula (I), where $R^2$ is $N(R^4)_2$ and $R^4$ is hydrogen and cyclohexyl, which is optionally substituted with one or more hydroxyl. In still another embodiment of formula (I), $R^2$ is $N(R^4)_2$, wherein $R^4$ is hydrogen and

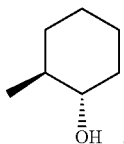

In another embodiment, for compounds of formula (I), A is selected from the group consisting of
  (1) phenyl,
  (2) pyridyl,
  (3) piperazinyl,
  (4) biphenyl, and
  (5) bipyridyl
wherein each is optionally substituted with one or more $R^a$.

In one embodiment, the invention is directed to methods of treating a patient (preferably a human) for diseases in which the M1 receptor is involved, such as Alzheimer's disease, cognitive impairment, schizophrenia, pain disorders and sleep disorders, by administering to the patient a therapeutically effective amount of a compound of general formula (I), or a pharmaceutically acceptable salt thereof, with one or more additional therapeutic agents, carriers, or diluents.

The invention is also directed to the use of a compound of formula (I) for treating diseases or disorders in which the M1 receptor is involved, such as Alzheimer's disease, cognitive impairment, schizophrenia, pain disorders and sleep disorders, by administering to the patient a compound of formula (I), or a pharmaceutically salt thereof, with one or more additional therapeutic agents, carriers, or diluents.

The invention is also directed to medicaments or pharmaceutical compositions for treating diseases or disorders in which the M1 receptor is involved, such as Alzheimer's disease, cognitive impairment, schizophrenia, pain disorders and sleep disorders, comprising a compound of formula (I), or a pharmaceutically acceptable salt thereof, and one or more additional therapeutic agents, carriers, or diluents.

The invention is further directed to a method for the manufacture of a medicament or a composition for treating diseases or disorders in which the M1 receptor is involved, such as Alzheimer's disease, cognitive impairment, schizophrenia, pain disorders and sleep disorders, comprising combining a compound of formula (I), or a pharmaceutically acceptable salt thereof, with one or more additional therapeutic agents, carriers, or diluents.

Specific embodiments of formula (I) are described in Examples 1-12, including:
1-Methoxy-4-(4-methoxybenzyl)-2-naphthoic acid;
1-Methoxy-4-[4-(1H-pyrazol-1-yl)benzyl]-2-naphthoic acid;
4-[(6-Chloropyridin-3-yl)methyl]-N-[(1S,2S)-2-hydroxycyclohexyl]-1-methoxy-2-naphthamide;
N-[(1S,2S)-2-Hydroxycyclohexyl]-1-methoxy-4-[(6-methylpyridin-3-yl)methyl-2-naphthamide;
N-[(1S,2S)-2-Hydroxycyclohexyl]-1-methoxy-4-{[6-(1-methyl-1H-pyrazol-4-yl)pyridine-3-yl]methyl}-2-naphthamide;
1-Hydroxy-N-[(1S,2S)-2-hydroxycyclohexyl]-4-{[6-(1H-pyrazol-1-yl)pyridine-3-yl]methyl}-2-naphthamide;
N-[(1S,2S)-2-Hydroxycyclohexyl]-1-methoxy-4-{[6-(1H-pyrazol-1-yl)pyridine-3-yl]methyl}-2-naphthamide;
N-[(1S,2S)-2-Hydroxycyclohexyl]-1-methoxy-4-{[4-(1-methyl-1H-pyrazol-4-yl)piperazin-1-yl]methyl}-2-naphthamide;
N-[(1S,2S)-2-Hydroxycyclohexyl]-1-methoxy-4-[(6-vinylpyridin-3-yl)methyl]-2-naphthamide;

4-[(6-Chloropyridin-3-yl)methyl]-N-[(3R,4S)-3-hydroxytetrahydro-2H-pyran-4-yl]-1-methoxy-2-naphthamide;
N-[(1S,2S)-2-Hydroxycyclohexyl]-1-methoxy-4-{[2-(methylthio)pyridin-4-yl]methyl}-2-naphthamide; and
4-[(6-Chloropyridin-3-yl)methyl]-1-ethoxy-N-(1S,2S)-2-hydroxycyclohexyl]-2-naphthamide.

Within the genus of compounds of formula (I), there is a sub-genus of compounds of formula (II),

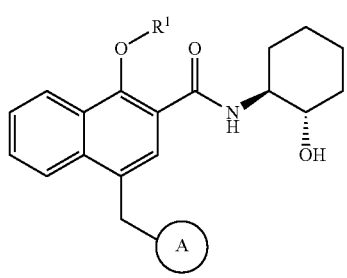

(II)

or a pharmaceutically acceptable salt thereof, wherein $R^1$ and A are as described above.

In one embodiment of compounds of formula (II), $R^1$ is selected from the group consisting of
(1) hydrogen,
(2) methyl,
(3) ethyl,
(4) —$C_{2-6}$ alkenyl, and
(5) —$C(O)N(R^4)_2$,
wherein each is optionally substituted with one or more $R^a$.

In another embodiment, compounds of formula (II), $R^1$ is hydrogen. In still another embodiment, compounds of formula (II), $R^1$ is methyl.

In another embodiment of compounds of formula (II), A is selected from the group consisting of
(1) phenyl,
(2) pyridyl,
(3) piperazinyl,
(4) biphenyl, and
(5) bipyridyl
wherein each is optionally substituted with one or more $R^a$.

In another embodiment of compounds of formula (II), A is

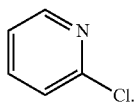

The invention is also directed to methods of treating a patient (preferably a human) for diseases or disorders in which the M1 receptor is involved, such as Alzheimer's Disease, cognitive impairment, schizophrenia, pain disorders and sleep disorders, by administering to the patient a therapeutically effective amount of a compound of formulae (II)-(IV), or a pharmaceutically acceptable salt thereof, with one or more additional therapeutic agents, carriers, or diluents.

The invention is also directed to the use of a compound of formulae (II)-(IV), for treating a disease or disorder in which the M1 receptor is involved, such as Alzheimer's Disease, cognitive impairment, schizophrenia, pain disorders and sleep disorders, by administering to the patient a compound of formulae (II)-(IV), or a pharmaceutically acceptable salt thereof, with one or more additional therapeutic agents, carriers, or diluents.

The invention is also directed to medicaments or pharmaceutical compositions for the treatment of diseases or disorders in a patient (preferably a human) in which the M1 receptor is involved, such as Alzheimer's Disease, cognitive impairment, schizophrenia, pain disorders, and sleep disorders, comprising a compound of formulae (II)-(IV), or a pharmaceutically acceptable salt thereof, and one or more additional therapeutic agents, carriers, or diluents.

The invention is also directed to a method for the manufacture of a medicament or a pharmaceutical composition for treating diseases in which M1 receptor is involved, such as Alzheimer's Disease, cognitive impairment, schizophrenia, pain disorders, and sleep disorders, comprising a compound of formulae (II)-(IV), or a pharmaceutically acceptable salt thereof, with one or more additional therapeutic agents, carriers, or diluents.

Examples of compounds of the invention in Table 1, of Formula (III) wherein $R^2$ and A are as indicated, were prepared according to the referenced procedure in the Examples that follow. The starting materials are either commercially available or known in the literature, or may be prepared from commercially available reagents using conventional reactions well known in the art.

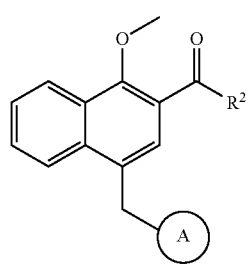

III

TABLE 1

| Compound Number | A | $R^2$ | M1 IP Value (nM) | LRMS | Method |
|---|---|---|---|---|---|
| 1-1 |  | OH | 872 | 369.1 | Example 2 |

TABLE 1-continued

| Compound Number | A | R² | M1 IP Value (nM) | LRMS | Method |
|---|---|---|---|---|---|
| 1-2 | 4-methyl-N-acetylanilinyl | OH | 1549 | 350.1 | Example 2 |
| 1-3 | 5-methyl-2-(pyridin-3-yl)pyridinyl | trans-2-hydroxycyclohexylamino | 24 | 467.9 | Example 5 |
| 1-4 | 1-methyl-4-cyano-4-(4-methylpyridin-2-yl)piperidinyl | OH | 5377 | 416.3 | Example 8 |
| 1-5 | 1-methyl-4-cyano-4-(4-methylpyridin-2-yl)piperidinyl | trans-2-hydroxycyclohexylamino | 104 | 513.4 | Example 8 |
| 1-6 | 3-(piperazin-1-yl)isoquinolinyl | trans-2-hydroxycyclohexylamino | 4015 | 525.5 | Example 8 |
| 1-7 | 5-methyl-2-methoxypyridinyl | trans-2-hydroxycyclohexylamino | 280 | 421.4 | Example 6 |
| 1-8 | 5-methyl-2-(5-formyloxypentanoyl)pyridinyl | trans-2-hydroxycyclohexylamino | 430 | 519.4 | Example 8 |
| 1-9 | 5-methyl-2-(methylthio)pyridinyl | trans-2-hydroxycyclohexylamino | 169 | 437.1 | Example 11 |

TABLE 1-continued

| Compound Number | A | R² | M1 IP Value (nM) | LRMS | Method |
|---|---|---|---|---|---|
| 1-10 | 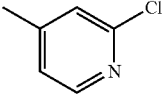 | 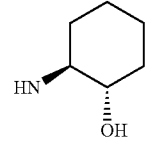 | 204 | 425.3 | Example 2/3 |
| 1-11 | 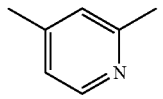 | 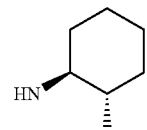 | 224 | 405.1 | Example 4 |
| 1-12 | 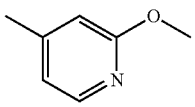 | 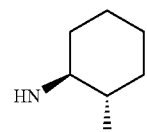 | 140 | 421.1 | Example 2/3 |
| 1-13 | 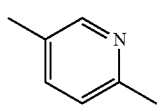 | 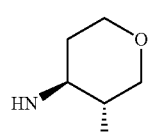 | 87 | 407.0 | Example 4/10 |
| 1-14 | 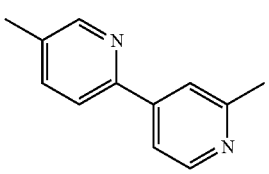 | 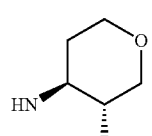 | 6.8 | 484.0 | Example 5/10 |
| 1-15 | 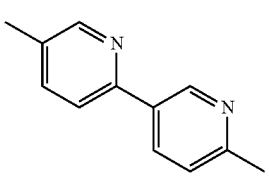 | 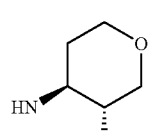 | 22 | 484.0 | Example 5/10 |

Examples of compounds of the invention in Table 2, of Formula (IV) wherein R¹ is as indicated, were prepared according to the referenced procedure in the Examples that follow. The starting materials are either commercially available or known in the literature, or may be prepared from commercially available reagents using conventional reactions well known in the art.

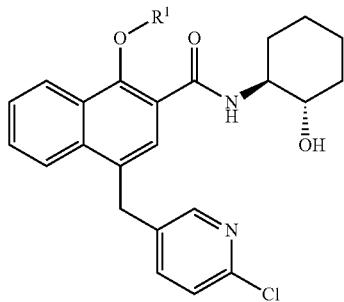

IV

TABLE 2

| Compound Number | R¹ | M1 IP Value (nM) | LRMS | Method |
|---|---|---|---|---|
| 2-1 | H | 9083 | 411.3 | Example 1 |
| 2-2 | ~~/~~\\~~//~~ | 1140 | 451.3 | Example 12 |
| 2-3 | (CH₃C(O)NHCH₂CH₂-) | 5016 | 481.9 | Example 12 |

Where a variable occurs more than once in any of formulae (I)-(IV), or in a substituent thereof, the individual occurrences of that variable are independent of each other, unless otherwise specified.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

The term heterocycle, heterocyclyl, or heterocyclic, as used herein, represents a stable 5- to 7-membered monocyclic non-aromatic ring or a stable 8- to 11-membered bicyclic non- or partially-aromatic ring and which consists of carbon atoms and from one to four heteroatoms selected from the group consisting of N, O, and S. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, triazolyl and thienyl.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl. The term "aryl" also includes fused cyclic hydrocarbon rings which are partially aromatic (i.e., one of the fused rings is aromatic and the other is non-aromatic). An exemplary aryl group which is partially aromatic is indanyl.

As used herein, the term "heteroaryl," by itself or as part of another substituent, means a cyclic or polycyclic group having from five to twelve ring atoms selected from C, O, N, N→O, C=O and S, wherein at least one ring heteroatom is O, N, N→O or S, and wherein at least one of the constituent rings is aromatic. Exemplary heteroaryl groups for use in the invention include carbazolyl, carbolinyl, chromenyl, cinnolinyl, furanyl, benzofuranyl, benzofurazanyl, isobenzofuranyl, imidazolyl, benzimidazolyl, benzimidazolonyl, indazolyl, indolyl, isoindolyl, indolinyl, indolazinyl, indynyl, oxadiazolyl, oxazolyl, benzoxazolyl, isoxazolyl, pyranyl, pyrazinyl, pyrazolyl, benzopyrazolyl, pyridazinyl, pyridyl, pyrimidinyl, pyrrolyl, quinolyl, isoquinolyl, tetrazolyl, thiazolyl, isothiazolyl, thiadiazolyl, thienyl, benzothienyl, benzothiazolyl, quinoxalinyl, triazinyl and triazolyl, and N-oxides thereof.

One subgroup of heteroaryl groups have 5 ring atoms. Exemplary heteroaryl groups in this embodiment are pyrazolyl, pyrrolyl and imidazolyl.

Another subgroup of heteroaryl groups have 6 ring atoms. Exemplary heteroaryl groups in this embodiment are pyridyl, pyridyl N-oxide and pyrimidyl.

The term "heteroaryl" also includes fused cyclic heterocyclic rings which are partially aromatic (i.e., one of the fused rings is aromatic and the other is non-aromatic). An exemplary heteroaryl group which is partially aromatic is benzodioxol.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formulae (I) to (IV).

Formulae (I)-(IV) are shown above without a definite stereochemistry. The present invention includes all stereoisomers of formulae (I)-(IV), and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The compounds of the invention may be prepared according to the following reaction schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

The present invention also provides a method for the synthesis of compounds useful as intermediates in the preparation of compounds of the invention as shown in the Examples that follow.

During any of the above synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P. G. M. Wuts, *Protective Groups in Organic Synthesis*, John Wiley & Sons, 1999. The protecting groups may be removed at a convenient sequent stage using methods known from the art.

Specific embodiments of the compounds of the invention, and methods of making them, are described in the Examples herein.

In the compounds of formulae (I)-(IV), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formulae (I)-(IV). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formulae (I)-(IV) can be prepared without undue experimentation by conventional techniques well known to those skilled in the art or by processes analogous to those described in the schemes and Examples herein using appropriate isotopically-enriched reagents and/or intermediates.

The term "substantially pure" means that the isolated material is at least 90% pure, and preferably 95% pure, and even more preferably 99% pure as assayed by analytical techniques known in the art.

As used herein, the term "muscarinic M1 receptor" refers to one of the five subtypes of the muscarinic acetylcholine receptor, which is from the superfamily of G-protein coupled receptors. The family of muscarinic receptors is described, for example, in *Pharmacol Ther.*, 1993, 58:319-379; *Eur. J. Pharmacol.*, 1996, 295:93-102, and *Mol. Pharmacol.*, 2002, 61:1297-1302. The muscarinic receptors are known to contain one or more allosteric sites, which may alter the affinity with which muscarinic ligands bind to the primary binding or orthosteric sites. See, for example, S. Lazareno et al, *Mol. Pharmacol.*, 2002, 62:6, 1491-1505.

As used herein, the terms "positive allosteric modulator" and "allosteric potentiator" are used interchangeably, and refer to a ligand which interacts with an allosteric site of a receptor to activate the primary binding site. The compounds of the invention are positive allosteric modulators of the muscarinic M1 receptor. For example, a modulator or potentiator may directly or indirectly augment the response produced by the endogenous ligand (such as acetylcholine) at the orthosteric site of the muscarinic M1 receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al., *Life Sciences*, 2001, 68:2517-2524. For a general description of the role of allosteric binding sites, see Christopoulos, *Nature Reviews: Drug Discovery*, 2002, 1:198-210.

It is believed that the compounds of the invention bind to an allosteric binding site that is distinct from the orthosteric acetylcholine site of the muscarinic M1 receptor, thereby augmenting the response produced by the endogenous ligand acetylcholine at the orthosteric site of the M1 receptor. It is also believed that the compounds of the invention bind to an allosteric site which is distinct from the xanomeline site of the muscarinic M1 receptor, thereby augmenting the response produced by the endogenous ligand acetylcholine at the orthosteric site of the M1 receptor.

It will be understood that, as used herein, references to the compounds of formulae (I)-(IV) are meant to also include the pharmaceutically acceptable salts, and also salts that are not pharmaceutically acceptable when they are used as precursors to the free compounds or in other synthetic manipulations.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulae (I)-(IV), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

Exemplifying the invention are the specific compounds of formulae (I)-(IV) disclosed herein that can be used as M1 allosteric modulators in a patient or subject such as a mammal in need of such activity, comprising the administration of an effective amount of the compound. In addition to humans, a variety of other mammals can be treated according to the method of the present invention.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compounds of the invention have utility in treating or ameliorating Alzheimer's disease. The compounds may also be useful in treating or ameliorating other diseases mediated by the muscarinic M1 receptor, such as schizophrenia, sleep disorders, pain disorders (including acute pain, inflammatory pain and neuropathic pain) and cognitive disorders (including mild cognitive impairment). Other conditions that may be treated by the compounds of the invention include Parkinson's Disease, pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prior disorders, amyotrophic lateral sclerosis, progressive supranuclear palsy, head trauma, stroke, pancreatitis, inclusion body myositis, other peripheral amyloidoses, diabetes, autism and atherosclerosis.

In certain embodiments, the compounds of the invention are useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type. In general, Alzheimer's Disease symptoms include confusion, irritability and aggression, mood swings, language breakdown, long-term memory loss, and the general withdrawal of the sufferer as their senses decline. The language problems associated with Alzheimer's Disease include a shrinking vocabulary and decreased word fluency. Alzheimer's Disease also includes impairment of fine motor tasks, such as writing, drawing, dressing and other coordinated movements. Alzheimer's Disease symptoms include apraxia (difficulties in movement planning).

Early stage Alzheimer's Disease is characterized by confusion, memory loss and changes in other cognitive abilities. Symptoms may include getting lost, trouble handling money and paying bills, repeating questions, taking longer to complete normal daily tasks, poor judgment, and mood and personality changes.

Intermediate stage Alzheimer's Disease is manifested by problems with reasoning, sensory processing, and conscious thought. Intermediate stage symptoms include continuing memory loss and confusion. Intermediate stage patients typically begin to have problems recognizing family and friends. Symptoms include the inability to learn new things, carry out tasks that involve multiple steps (such as getting dressed), or coping with new situations. Intermediate stage patients may have hallucinations, delusions, and paranoia, and may behave impulsively.

Patients suffering from severe Alzheimer's Disease are typically unable to communicate and are completely dependent on others for their care.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketanine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

In another specific embodiment, the invention provides a method for treating schizophrenia or psychosis comprising administering to a patient in need thereof an effective amount of a compound of formulae (I)-(IV) of the invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The present invention is further directed to a method for the manufacture of a medicament for treating or ameliorating Alzheimer's disease and other diseases mediated by the muscarinic M1 receptor, including those disorders and conditions listed above, in humans and animals comprising combining a compound of the present invention with one or more additional therapeutic agents, carriers, or diluents.

The present invention is further directed to compounds of the invention for use in the treatment of or to ameliorate Alzheimer's disease and other diseases mediated by the muscarinic M1 receptor, including those disorders and conditions listed above, in humans and animals comprising combining a compound of the present invention with one or more additional therapeutic agents, carriers, or diluents.

The subject or patient to whom the compounds of the present invention is administered is generally a human being, male or female, in whom M1 allosteric modulation is desired, but may also encompass other mammals, such as dogs, cats, mice, rats, cattle, horses, sheep, rabbits, monkeys, chimpanzees or other apes or primates, for which treatment of the above noted disorders is desired.

The compounds of the invention are further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned disease, disorders and conditions in combination with other agents. The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention include combinations with anti-Alzheimer's Disease agents, for example beta-secretase inhibitors; alpha 7 nicotinic agonists; ADAM 10 ligands or activators; gamma-secretase inhibitors; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists; 5-HT6 antagonists; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab; anti-inflammatory compounds such as R-flurbiprofen, nitroflurbiprofen; PPAR gamma agonists, such as pioglitazone and rosiglitazone; CB-1 receptor antagonists or CB-1 receptor inverse agonists; antibiotics such as doxycycline and rifampin; N-methyl-D-aspartate (NMDA) receptor antagonists, such as memantine and neramexane; cholinesterase inhibitors such as galantamine, rivastigmine, donepezil, tacrine, phenserine and ladostigil; growth hormone secretagogues such as ibutamoren, ibutamoren mesylate, and capromorelin; histamine $H_3$ receptor antagonists; AMPA agonists or AMPA modulators; PDE IV inhibitors; PDE10A inhibitors; $GABA_A$ inverse agonists; GSK3β inhibitors; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds include combinations with agents for the treatment of pain, for example non-steroidal anti-inflammatory agents, such as aspirin, diclofenac, diflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib and valdecoxib; CB-2 agonists; VR-1 antagonists; bradykinin B1 receptor antagonists; sodium channel blockers and antagonists; nitric oxide synthase (NOS) inhibitors (including iNOS and nNOS inhibitors); glycine site antagonists, including lacosamide; neuronal nicotinic agonists; NMDA antagonists; potassium channel openers; AMPA/kainate receptor antagonists; calcium channel blockers, such as ziconotide; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists; alpha agonists; neuronal nicotinic agonists; NMDA receptor agonists or antagonists; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, clonazepam, cyprazepam, desipramine, dexclamol, diazepam, dichloralphenazone, divalproex, diphenhydramine, doxepin, EMD-281014, eplivanserin, estazolam, eszopiclone, ethchlorvynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone, MOA-B inhibitors, antioxidants, A2a adenosine receptor antagonists, cholinergic agonists and dopamine receptor agonists such as alentemol, bromocriptine, fenoldopam, lisuride, naxagolide, pergolide and pramipexole.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of Examples 1-12 had M1 activity in a FLIPR assay as shown in Table 3. Active compounds have a M1 potential ranging from 10 to 30000 nM.

TABLE 3

| Example Number | M1 Potential (nM) |
|---|---|
| 1 | 3322 |
| 2 | 574 |
| 3 | 260 |
| 4 | 121 |
| 5 | 17 |
| 6 | 4710 |
| 7 | 82 |
| 8 | 3879 |
| 9 | 190 |

TABLE 3-continued

| Example Number | M1 Potential (nM) |
|---|---|
| 10 | 56 |
| 11 | 281 |
| 12 | 985 |

EXAMPLES

The following abbreviations are used herein: Me: methyl; Et: ethyl; Bu: butyl; t-Bu: tert-butyl; Ar: aryl; Ph: phenyl; Bn: benzyl; Ac: acetyl; DMF.DMA: N,N-dimethylformamide dimethyl acetal; DMSO: dimethylsulfoxide; DMF: N,N-dimethylformamide; DMEM: Dulbecco's Modified Eagle Medium (High Glucose); FBS: fetal bovine serum; dppf: (diphenylphosphino)ferrocene; THF: tetrahydrofuran; TEA: triethylamine; BOP: benzotriazolyloxytris(dimethylamino) phosphonium hexafluorophosphate; DCE: dichloroethane; LDH: lactate dehydrogenase; m-CPBA: meta-chloroperbenzoic acid; NADP: nicotinamide adenine dinucleotide phosphate; KRED: ketoreductase; NAD: nicotinamide adenine dinucleotide; MtBE: methyl tert-butyl ether; TBAI: tetra-butyl ammonium iodide; rt: room temperature; aq: aqueous; HPLC: high performance liquid chromatography; MS: mass spectrometry, [CDX TA P1G5, GDH-103, and KRED-130—obtained from Codex Transaminase panel enzyme P1G5 (commercially available from Codex (Redwood City, Calif., USA) panel products].

Several methods for preparing the compounds of this invention are illustrated in the schemes and examples herein. Starting materials are made according to procedures known in the art or as illustrated herein. The following examples are provided so that the invention might be more fully understood.

Example 1

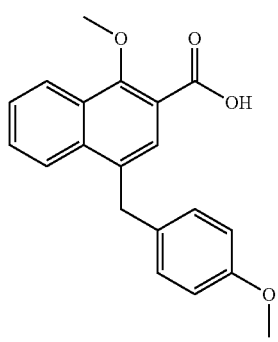 [SMILES: COc1ccc(Cc2cc(C(=O)O)c(OC)c3ccccc23)cc1]

1-Methoxy-4-(4-methoxybenzyl)-2-naphthoic acid

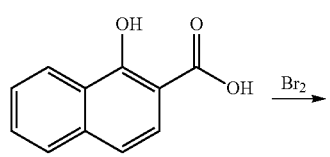

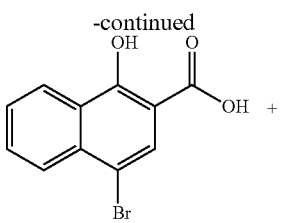

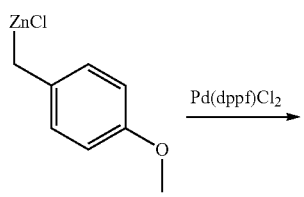

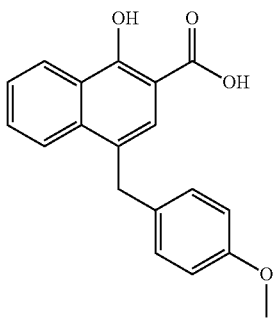

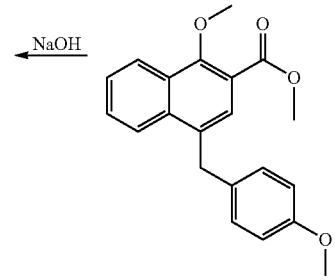

To a solution of 1-hydroxy-2-naphthoic acid (10.2 g, 53.9 mmol) in 100 mL of acetic acid was added bromine (6.60 mL, 53.9 mmol) dropwise. After 72 hours, the reaction was filtered and the filter cake was washed with acetic acid (40 mL) and hexanes (150 mL) to provide 4-bromo-1-hydroxy-2-naphthoic acid that gave a proton NMR spectra consistent with theory.

To a solution of the above compound (0.325 g, 1.22 mmol) in 3 mL of THF under an atmosphere of nitrogen was added 4-methoxybenzylzinc chloride (0.5 M in THF, 4.87 mL, 2.43 mmol) and [1,1'-bis(diphenylphosphino)ferrocene]dichloropalladium(II), 1:1 complex with dichloromethane (0.099 g, 0.12 mmol). The reaction was heated at 65° C. for 2 hours, then cooled to room temperature and concentrated in vacuo. The residue was purified via preparative reverse phase HPLC to provide 1-hydroxy-4-(4-methoxybenzyl)-2-naphthoic acid that gave a proton NMR spectra consistent with theory and a mass ion (ES+) of 309.1 for [M+H]+.

To a solution of the above compound (0.111 g, 0.360 mmol) in 10 mL of acetone was added dimethyl sulfate (0.10 mL, 1.1 mmol) and potassium carbonate (0.174 g, 1.26 mmol). The reaction was heated to reflux for 14 hours, cooled to room temperature, filtered, and concentrated in vacuo. The residue was purified via silica gel chromatography, eluting with 0-20% ethyl acetate in hexanes to provide methyl 1-methoxy-4-(4-methoxybenzyl)-2-naphthoate that gave a proton NMR spectra consistent with theory and a mass ion (ES+) of 336.9 for [M+H]+.

To a solution of the above compound (0.085 g, 0.25 mmol) in a mixture of 1 mL of methanol and 6 mL of THF was added aqueous sodium hydroxide (1.0 M, 0.30 mL, 0.30 mmol). After 72 hours, the reaction was acidified with 12 N HCl and concentrated in vacuo. The residue was purified via preparative reverse phase HPLC to provide the title compound that gave a proton NMR spectra consistent with theory and a mass ion (ES+) of 323.2 for [M+H]+: $^1$H NMR (400 MHz, CDCl$_3$) δ 8.23 (d, J=7.6 Hz, 1H), 8.09 (d, J=7.6 Hz, 1H), 7.64-7.59 (m, 3H), 7.15 (d, J=8.5 Hz, 2H), 6.84 (d, J=8.8 Hz, 2H), 4.33 (s, 2H), 3.95 (s, 3H), 3.69 (s, 3H).

Example 2

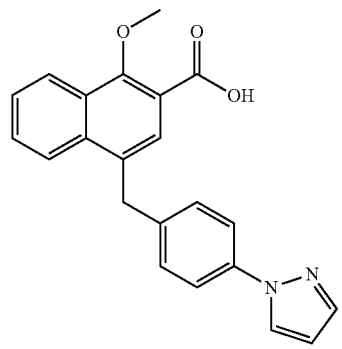 [SMILES: COc1c(C(=O)O)cc(Cc2ccc(-n3cccn3)cc2)c2ccccc12]

1-Methoxy-4-[4-(1H-pyrazol-1-yl)benzyl]-2-naphthoic acid

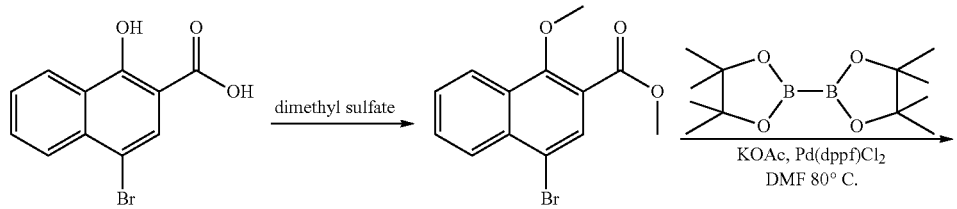

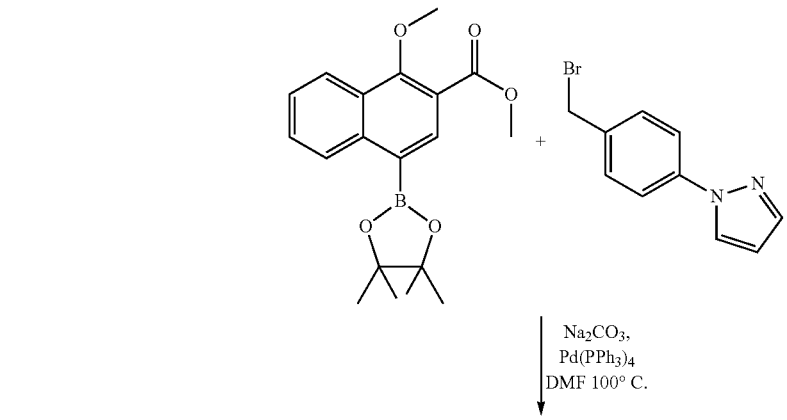

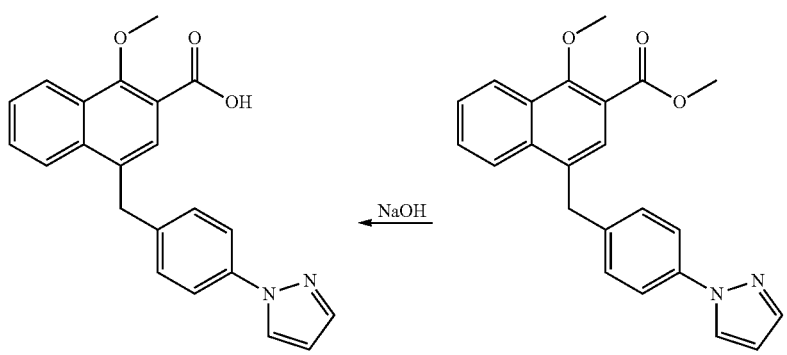

To a solution of 4-bromo-1-hydroxy-2-naphthoic acid (see Example 1, 1.63 g, 6.10 mmol) in 35 mL of acetone was added dimethyl sulfate (1.75 mL, 18.3 mmol) and potassium carbonate (2.95 g, 21.4 mmol). The reaction was heated to reflux for 14 hours, cooled to room temperature, filtered, and concentrated in vacuo. The residue was purified via silica gel chromatography, eluting with 0-20% ethyl acetate in hexanes to provide methyl 4-bromo-1-methoxy-2-naphthoate that gave a proton NMR spectra consistent with theory.

To a solution of the above compound (0.447 g, 1.52 mmol) in 10 mL of DMSO under an atmosphere of nitrogen was added potassium acetate (0.446 g, 4.54 mmol), bis(pinacolato) diboron (0.423 g, 1.67 mmol), and [1,1'-bis(diphenylphosphino)ferrocene]dichloro-palladium(II), 1:1 complex with dichloromethane (0.124 g, 0.151 mmol). The mixture was heated at 80° C. for 3 hours, cooled to room temperature, and diluted with water and extracted 3× with ethyl acetate. The combined organic fractions were dried over sodium sulfate, filtered, and concentrated in vacuo to provide methyl 1-methoxy-4-(4,4,5,5-tetramethyl-1,3,2-dioxaborolan-2-yl)-2-naphthoate that gave a proton NMR spectra consistent with theory.

To a solution of the above compound (0.118 g, 0.345 mmol) in 4 mL of DMF under an atmosphere of nitrogen was added 1-[4-(bromomethyl)phenyl]-1H-pyrazole (0.082 g, 0.34 mmol), sodium carbonate (0.219 g, 2.07 mmol), and tetrakis(triphenylphosphine)palladium (0) (0.040 g, 0.034 mmol). The mixture was heated at 100° C. for 5 hours, cooled to room temperature, diluted with water, and extracted 2× with ethyl acetate. The combined organic fractions were dried over sodium sulfate, filtered, and concentrated in vacuo. The residue was purified via silica gel chromatography, eluting with 0-50% ethyl acetate in hexanes to provide methyl 1-methoxy-4-[4-(1H-pyrazol-1-yl)benzyl]-2-naphthoate that gave proton NMR spectra consistent with theory and a mass ion (ES+) of 373.2 for [M+H]$^+$.

To a solution of the above compound (0.044 g, 0.12 mmol) in a mixture of 5 mL of THF was added aqueous sodium hydroxide (1.0 M, 0.12 mL, 0.12 mmol). After 18 hours, the reaction was acidified with 12 N HCl and concentrated in vacuo. The residue was purified via preparative reverse phase HPLC to provide the title compound that gave a proton NMR spectra consistent with theory and a mass ion (ES+) of 359.1 for [M+H]$^+$: $^1$H NMR (400 MHz, d$_6$-DMSO) δ 13.0 (s, 1H), 8.41 (s, 1H), 8.24 (d, J=7.3 Hz, 1H), 8.10 (d, J=7.3 Hz, 1H), 7.74-7.60 (m, 6H), 7.35 (d, J=8.5 Hz, 2H), 6.50 (s, 1H), 4.45 (s, 2H), 3.97 (s, 3H).

Example 3

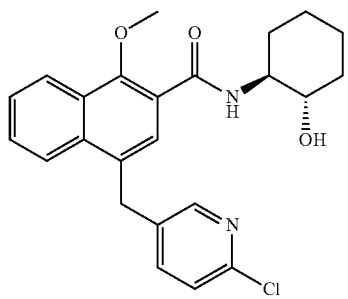 [SMILES: COc1c(C(=O)N[C@H]2CCCC[C@@H]2O)cc(Cc2ccc(Cl)nc2)c2ccccc12]

4-[(6-Chloropyridin-3-yl)methyl]-N-[(1S,2S)-2-hydroxycyclohexyl]-1-methoxy-2-naphthamide

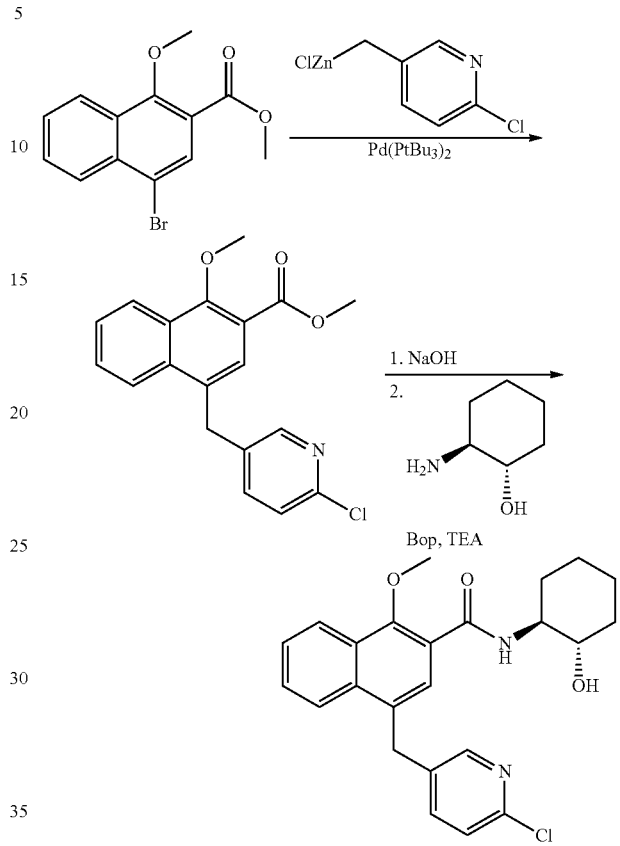

To a solution of methyl 4-bromo-1-methoxy-2-naphthoate (see Example 2, 0.500 g, 1.69 mmol) in 5 mL of THF under an atmosphere of nitrogen was added (2-chloro-5-pyridyl)methylzinc chloride (0.5 M in THF, 10.2 mL, 5.08 mmol) and tetrakis(triphenylphosphine)palladium (0) (0.050 g, 0.043 mmol). The reaction was heated at 90° C. for 2 hours, then cooled to room temperature and diluted with water and ethyl acetate. The mixture was filtered through celite and the organic solution was washed with brine, dried over sodium sulfate, filtered, and concentrated in vacuo. The residue was purified via silica gel chromatography, eluting with 0-20% ethyl acetate in hexanes to provide methyl 4-[(6-chloropyridin-3-yl)methyl]-1-methoxy-2-naphthoate that gave a mass ion (ES+) of 342.0 for [M+H]$^+$.

To a solution of the above compound (0.300 g, 0.878 mmol) in 3 mL of THF was added aqueous sodium hydroxide (5.0 M, 1.76 mL, 8.78 mmol). The reaction was heated at 90° C. for 4 hours, then cooled to room temperature and acidified with 1 N HCl. The solution was extracted 3× with ethyl acetate and the combined organic fractions were washed with brine, dried over sodium sulfate, filtered, and concentrated in vacuo to provide 4-[(6-chloropyridin-3-yl)methyl]-1-methoxy-2-naphthoic acid that gave a proton NMR spectra consistent with theory and a mass ion (ES+) of 328.1 for [M+H]$^+$.

To a solution of the above compound (0.280 g, 0.854 mmol) in 5 mL of dichloromethane was added (1H-1,2,3-benzotriazol-1-yloxy) [tris(dimethylamino)]phosphonium hexafluorophosphate (0.756 g, 1.71 mmol), (1S,2S)-2-aminocyclohexanol (0.148 g, 1.28 mmol), and triethylamine (0.24 mL, 1.7 mmol). After 3 hours, the reaction was diluted with dichloromethane, washed with water and brine, dried over sodium sulfate, filtered, and concentrated in vacuo. The residue was purified via silica gel chromatography, eluting with 10-60% ethyl acetate in hexanes to provide the title compound that gave a proton NMR spectra consistent with theory and a mass ion (ES+) of 424.9 for [M+H]+: 1H NMR (400 MHz, CDCl3) δ 8.33 (s, 1H), 8.23-8.20 (m, 1H), 8.10 (d, J=7.0 Hz, 1H), 8.09-8.01 (m, 11H), 7.86-7.84 (m, 1H), 7.61-7.54 (m, 2H), 7.39-7.36 (m, 1H), 7.17 (d, J=7.7 Hz, 1H), 4.39 (s, 2H), 4.02 (s, 3H), 3.96 (br s, 1H), 3.54-3.48 (m, 2H), 2.16-2.13 (m, 2H), 1.83-1.79 (m, 2H), 1.50-1.25 (m, 3H).

Example 4

N-[(1S,2S)-2-Hydroxycyclohexyl]-1-methoxy-4-[(6-methylpyridin-3-yl)methyl-2-naphthamide

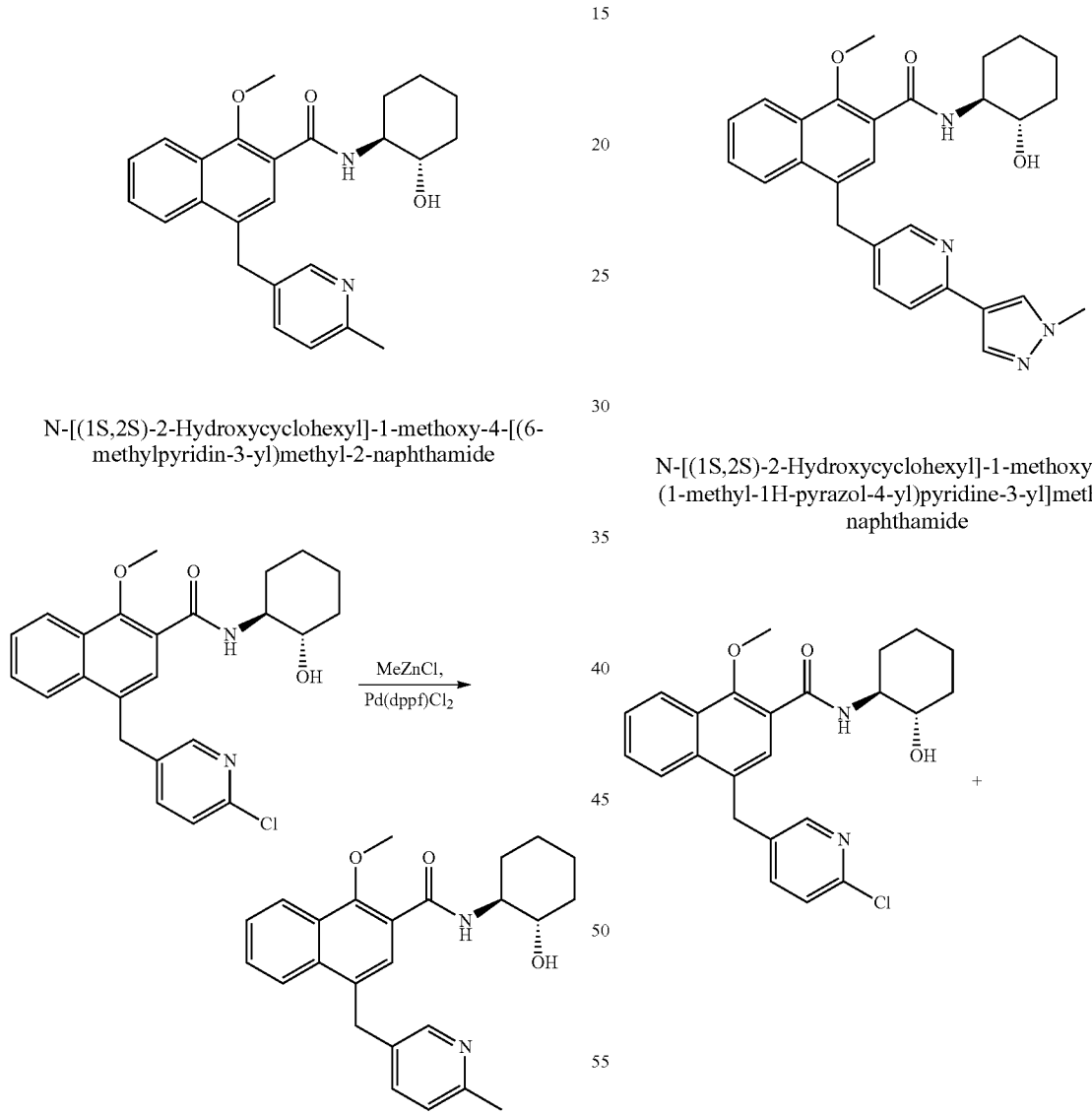

To a solution of 4-[(6-chloropyridin-3-yl)methyl]-N-[(1S,2S)-2-hydroxycyclohexyl]-1-methoxy-2-naphthamide, Example 3, (0.050 g, 0.12 mmol) in 3 mL of THF under an atmosphere of nitrogen was added methylzinc chloride (1.0 M in THF, 0.35 mL, 0.35 mmol) and [1,1'-bis-(diphenylphosphino)ferrocene]dichloro-palladium(II), 1:1 complex with dichloromethane (4.3 mg, 0.0059 mmol). The reaction was heated at 100° C. for 4 hours, then cooled to room temperature, treated with water, and concentrated in vacuo. The residue was purified via preparative reverse phase HPLC to provide the title compound that gave a proton NMR spectra consistent with theory and a mass ion (ES+) of 405.1 for [M+H]+: 1H NMR (400 MHz, CDCl3 δ 8.77 (br s, 1H), 8.25 (d, J=8.6 Hz, 1H), 8.16 (br s, 1H), 8.02-7.91 (m, 2H), 7.82 (d, J=7.0 Hz, 1H), 7.65-7.60 (m, 2H), 7.48 (d, J=8.2 Hz, 1H), 4.55 (s, 2H), 4.05 (s, 3H), 3.98 (s, 1H), 2.78 (s, 3H), 2.78-2.75 (m, 1H), 2.13-2.00 (m, 2H), 1.89-1.82 (m, 2H), 1.51-1.39 (m, 4H).

Example 5

N-[(1S,2S)-2-Hydroxycyclohexyl]-1-methoxy-4-{[6-(1-methyl-1H-pyrazol-4-yl)pyridine-3-yl]methyl}-2-naphthamide

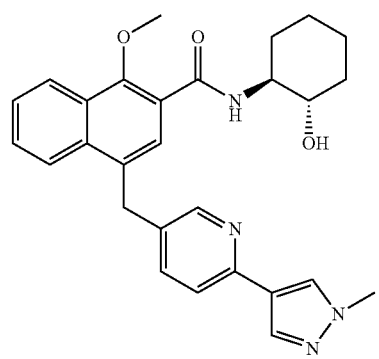 [SMILES: COc1c(C(=O)N[C@H]2CCCC[C@@H]2O)cc(Cc2ccc(-c3cnn(C)c3)nc2)c2ccccc12]

+

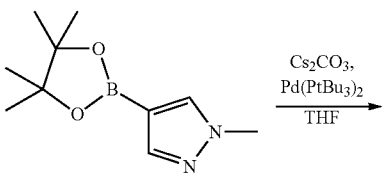

34

1-Hydroxy-N-[(1S,2S)-2-hydroxycyclohexyl]-4-{[6-(1H-pyrazol-1-yl)pyridine-3-yl]methyl}-2-naphthamide

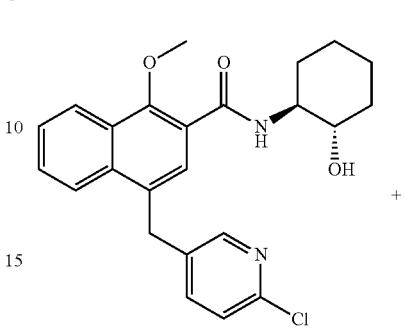

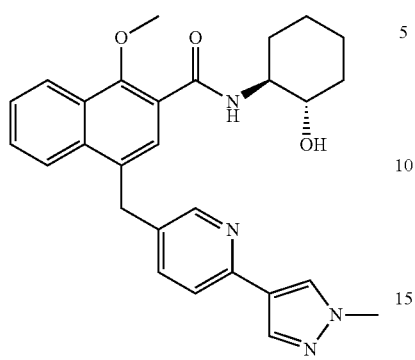

To a solution of 4-[(6-chloropyridin-3-yl)methyl]-N-[(1S,2S)-2-hydroxycyclohexyl]-1-methoxy-2-naphthamide (Example 3, 0.050 g, 0.12 mmol) in 3 mL of THF under an atmosphere of nitrogen was added aqueous cesium carbonate (1 M, 0.24 mL, 0.24 mmol), 1-methyl-4-(4,4,5,5-tetramethyl-1,3,2-dioxaborolan-2-yl)-1H-pyrazole (0.037 g, 0.18 mmol), and bis(tri-tert-butylphosphine)palladium(0) (4.0 mg, 0.0078 mmol). The reaction was heated at 100° C. for 16 hours, cooled to room temperature, and concentrated in vacuo. The residue was purified via preparative reverse phase HPLC to provide the title compound that gave a proton NMR spectra consistent with theory and a mass ion (ES+) of 470.9 for [M+H]$^+$: $^1$H NMR (400 MHz, CDCl$_3$) δ 8.84 (s, 1H), 8.59 (s, 1H), 8.26-8.23 (m, 1H), 8.12 (d, J=7.1 Hz, 1H), 8.07-7.89 (m, 3H), 7.85-7.82 (m, 1H), 7.70-7.61 (m, 3H), 4.52 (s, 2H), 4.04 (s, 3H), 4.00 (s, 3H), 3.98 (br s, 1H), 3.57-3.51 (m, 1H), 2.16-2.13 (m, 2H), 1.79 (br s, 2H), 1.50-1.21 (m, 4H).

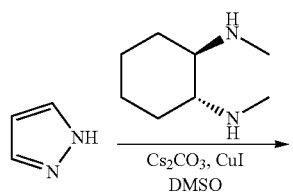

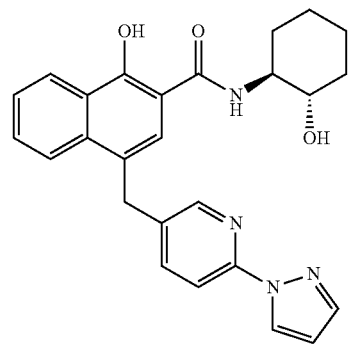

Example 6

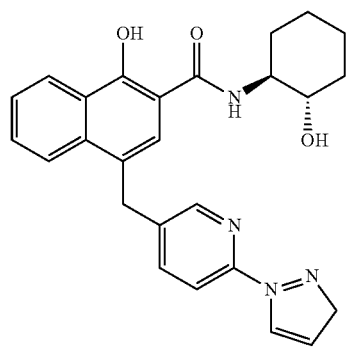

To a solution of 4-[(6-chloropyridin-3-yl)methyl]-N-[(1S,2S)-2-hydroxycyclohexyl]-1-methoxy-2-naphthamide (Example 3, 0.050 g, 0.12 mmol) and pyrazole (8.0 mg, 0.12 mmol) in 2 mL of DMSO under an atmosphere of nitrogen was added aqueous cesium carbonate (1 N, 0.23 mL, 1 N aqueous, 0.23 mmol), trans-N,N'-dimethylcyclohexane-1,2-diamine (2.2 mg, 0.015 mmol), and copper(I) iodide (1.4 g, 0.0076 mmol). The mixture was heated at 120° C. for 20 hours, cooled to room temperature, and additional trans-N,N'-dimethylcyclohexane-1,2-diamine (2.16 mg, 0.015 mmol) and copper(I) iodide (1.4 mg, 0.0076 mmol) were added. The reaction was heated at 140° C. for 24 hours, cooled to room temperature, filtered, and purified via preparative reverse phase HPLC to provide the title compound that gave a proton NMR spectra consistent with theory and a mass ion (ES+) of 442.9 for [M+H]$^+$: $^1$H NMR (400 MHz, CD$_3$OD) δ 8.50-8.47 (m, 2H), 8.33 (s, 1H), 7.84-7.81 (m, 1H), 7.76-7.74 (m, 2H), 7.60-7.51 (m, 2H), 7.24-7.20 (m, 2H), 6.48 (br s, 1H), 6.37 (d, J=6.2 Hz, 1H), 4.36 (s, 2H), 3.95-3.92 (m, 1H), 3.58-3.51 (m, 1H), 2.16-2.13 (m, 2H), 1.81-1.78 (m, 2H), 1.46-1.25 (m, 4H).

Example 7

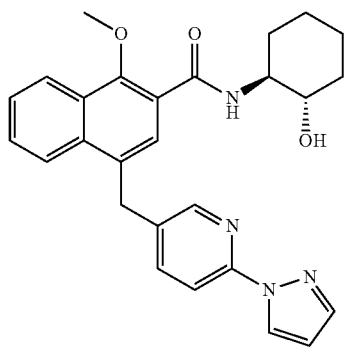 [SMILES: COc1c(C(=O)N[C@H]2CCCC[C@@H]2O)cc(Cc2ccc(-n3cccn3)nc2)c2ccccc12]

N-[(1S,2S)-2-Hydroxycyclohexyl]-1-methoxy-4-{[6-(1H-pyrazol-1-yl)pyridine-3-yl]methyl}-2-naphthamide

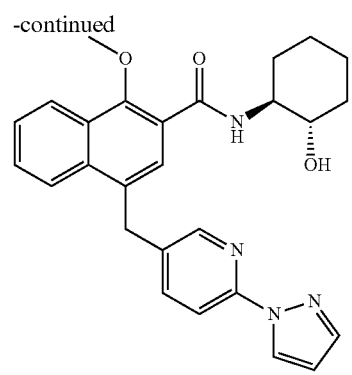

To a solution of 1-hydroxy-N-[(1S,2S)-2-hydroxycyclohexyl]-4-{[6-(1H-pyrazol-1-yl)pyridine-3-yl]methyl}-2-naphthamide (Example 6, 0.120 g, 0.271 mmol) in 4 mL of DMF was added potassium carbonate (0.041 g, 0.30 mmol) and iodomethane (0.042 g, 0.30 mmol). After 24 hours, the reaction was diluted with ethyl acetate, washed with water, dried over sodium sulfate, filtered, and concentrated in vacuo. The residue was purified via silica gel chromatography, eluting with 0-10% methanol in dichloromethane to provide the title compound that gave a proton NMR spectra consistent with theory and a mass ion (ES+) of 457.4 for [M+H]+: 1H NMR (400 MHz, CDCl3) δ 8.50 (br s, 1H), 8.30 (br s, 1H), 8.22-8.11 (m, 2H), 8.03 (s, 1H), 7.92 (d, J=6.9 Hz, 1H), 7.84 (br s, 1H), 7.70 (br s, 1H), 7.57 (br s, 2H), 6.44 (br s, 1H), 4.44 (s, 2H), 4.03 (s, 3H), 3.98 (br s, 1H), 3.53 (br s, 1H), 2.36-2.14 (m, 3H), 1.79 (br s, 2H), 1.47-1.26 (m, 3H).

Example 8

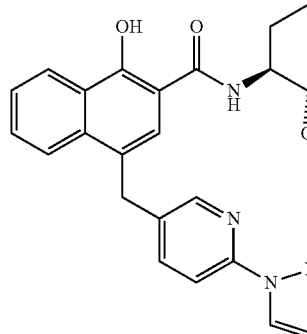

MeI, K2CO3 →

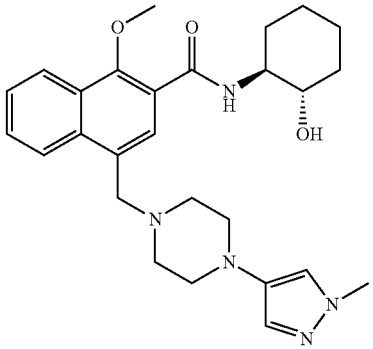 [SMILES: COc1c(C(=O)N[C@H]2CCCC[C@@H]2O)cc(CN2CCN(c3cnn(C)c3)CC2)c2ccccc12]

N-[(1S,2S)-2-Hydroxycyclohexyl]-1-methoxy-4-{[4-(1-methyl-1H-pyrazol-4-yl)piperazin-1-yl]methyl}-2-naphthamide

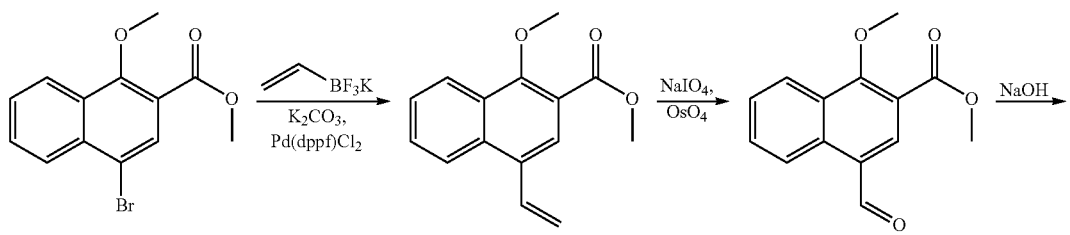

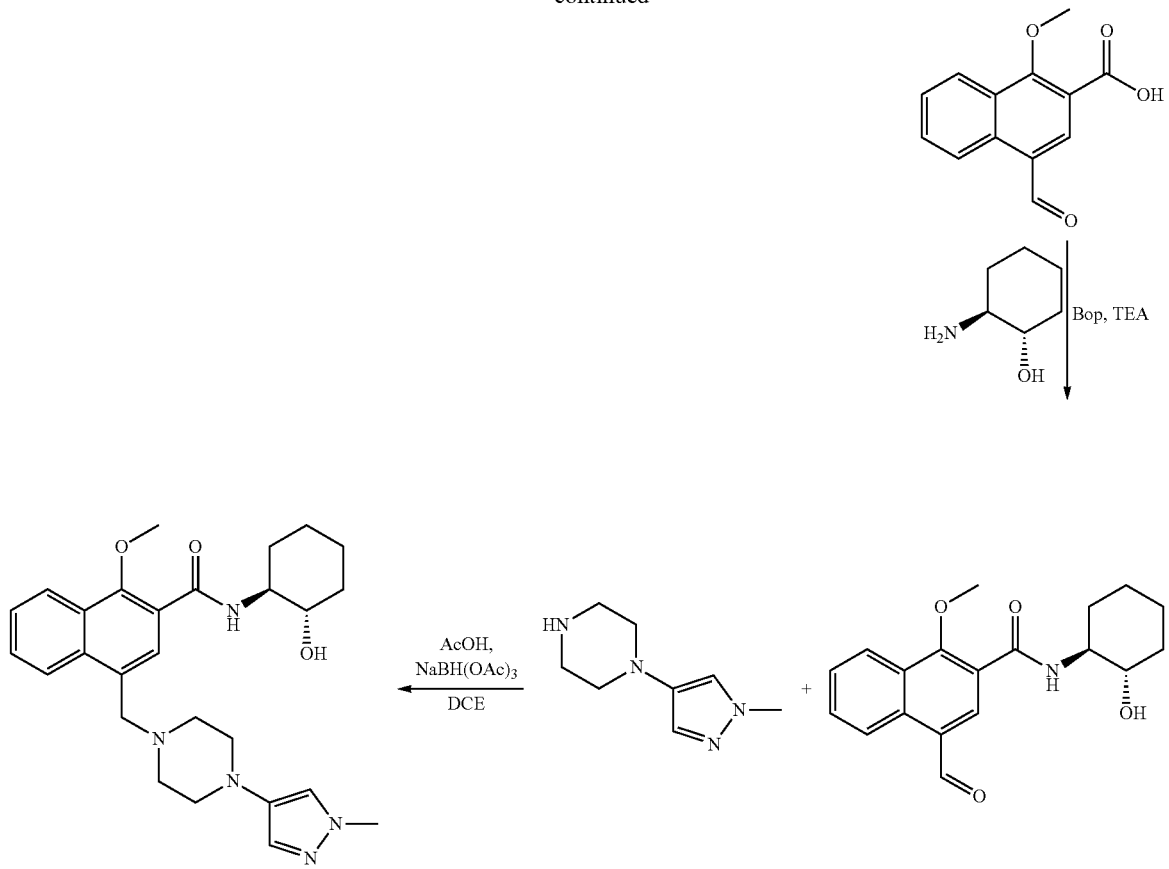

To a solution of methyl 4-bromo-1-methoxy-2-naphthoate (see Example 2, 5.00 g, 16.9 mmol) in a 105 mL of a 20:1 mixture of THF:water under an atmosphere of nitrogen was added potassium carbonate (2.58 g, 18.6 mmol), potassium vinyltrifluoroborate (3.40 g, 25.4 mmol), and [1,1'-bis(diphenylphosphino)ferrocene]dichloro-palladium(II), 1:1 complex with dichloromethane (1.24 g, 1.69 mmol). The reaction was heated at 65° C. for 65 hours, cooled to room temperature, diluted with ethyl acetate, and filtered through celite. The filtrate was concentrated in vacuo to provide methyl 4-formyl-1-methoxy-2-naphthoate that gave a mass ion (ES+) of 242.3 for [M+H]+.

To a solution of the above compound (4.10 g, 16.9 mmol) in a 200 mL of a 2:1:1 mixture of THF:acetone:water was added sodium periodate (10.9 g, 50.8 mmol) and osmium tetroxide (4% aqueous solution, 6.65 mL, 0.847 mmol) dropwise. After 2 hours, the reaction was diluted with ethyl acetate, washed with water, aqueous sodium thiosulfate, and brine. The organic solution was dried over sodium sulfate, filtered, and concentrated in vacuo. The residue was purified via silica gel chromatography, eluting with 0-20% ethyl acetate in hexanes to provide methyl 4-formyl-1-methoxy-2-naphthoate that gave a proton NMR spectra consistent with theory and a mass ion (ES+) of 245.2 for [M+H]+.

To a solution of the above compound (1.00 g, 4.09 mmol) in 30 mL of THF was added aqueous sodium hydroxide (5 M, 2.46 mL, 12.3 mmol). The reaction was heated to 50° C. for 65 hours, cooled to room temperature, and diluted with dichloromethane. The organic solution was acidified with 1 N HCl, and the resultant solid was collected via filtration to provide 4-formyl-1-methoxy-2-naphthoic acid that gave a proton NMR spectra consistent with theory and a mass ion (ES+) of 229.1 for [M+H]+.

To a solution of the above compound (0.700 g, 3.04 mmol) in 5 mL of DMF was added (1H-1,2,3-benzotriazol-1-yloxy)[tris(dimethylamino)]phosphonium hexafluorophosphate (2.69 g, 6.08 mmol), (1S,2S)-2-aminocyclohexanol (0.420 g, 3.65 mmol), and triethylamine (0.85 mL, 6.1 mmol). After 24 hours, the reaction was diluted with ethyl acetate, washed with water and brine, dried over sodium sulfate, filtered, and concentrated in vacuo. The residue was purified via silica gel chromatography, eluting with 40-100% ethyl acetate in hexanes to provide 4-formyl-N-[(1S,2S)-2-hydroxycyclohexyl]-1-methoxy-2-naphthamide that gave a proton NMR spectra consistent with theory and a mass ion (ES+) of 328.3 for [M+H]+.

To a solution of the above compound (0.040 g, 0.12 mmol) in 5 mL of 1,2-dichloroethane was added 1-(1-methyl-1H-pyrazol-4-yl)piperazine hydrochloride (0.037 g, 0.17 mmol), sodium triacetoxyborohydride (0.039 g, 0.18 mmol), acetic acid (0:035 mL, 0.61 mmol), and triethylamine (0.051 mL, 0.37 mmol). After 18 hours, the reaction was diluted with ethyl acetate, and washed 3× with water and 1× with brine. The organic solution was dried over sodium sulfate, filtered, and concentrated in vacuo. The residue was purified via preparative reverse phase HPLC to provide the title compound that gave a proton NMR spectra consistent with theory and a mass ion (ES+) of 478.5 for [M+H]+: 1H NMR (400 MHz, d6-DMSO) δ 9.71 (br s, 1H), 8.43 (d, J=8.4 Hz, 1H), 8.31-8.25 (m, 2H), 8.06 (s, 1H), 7.81-7.71 (m, 2H), 7.31 (s, 1H), 7.17 (s, 1H), 4.87 (s, 2H), 4.01 (s, 3H), 3.72 (s, 3H), 3.40 (br s, 8H), 2.79-2.76 (m, 2H), 2.05 (br s, 1H), 1.94-1.91 (m, 1H), 1.75-1.60 (m, 2H), 1.37-1.20 (m, 4H).

Example 9

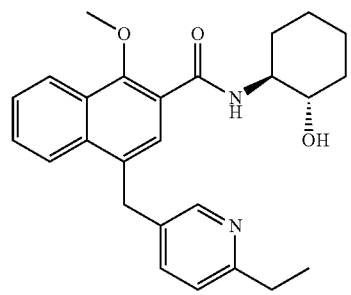 [SMILES: CCc1ccc(Cc2cc(C(=O)N[C@H]3CCCC[C@@H]3O)c(OC)c3ccccc23)cn1]

N-[(1S,2S)-2-Hydroxycyclohexyl]-1-methoxy-4-[(6-ethylpyridin-3-yl)methyl]-2-naphthamide

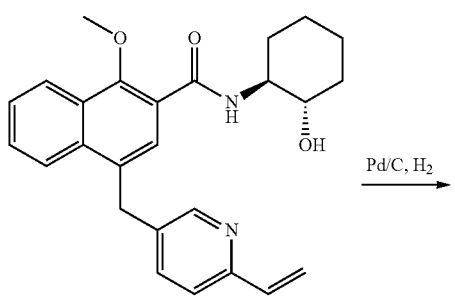

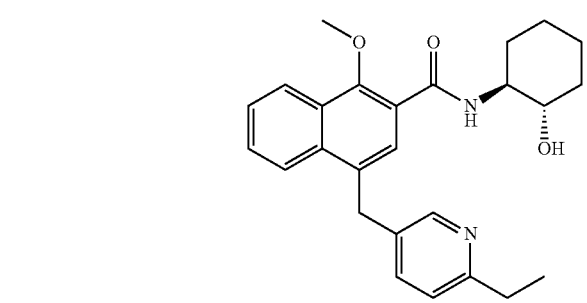

Example 9 was prepared by the procedure described for the synthesis of N-[(1S,2S)-2-hydroxycyclohexyl]-1-methoxy-4-{[6-(1-methyl-1H-pyrazol-4-yl)pyridine-3-yl]methyl}-2-naphthamide in Example 5, substituting potassium vinyltrifluoroborate for 1-methyl-4-(4,4,5,5-tetramethyl-1,3,2-dioxaborolan-2-yl)-1H-pyrazole.

To a solution of N-[(1S,2S)-2-hydroxycyclohexyl]-1-methoxy-4-[(6-vinylpyridin-3-yl)methyl]-2-naphthamide (0.050 g, 0.12 mmol) in 5 mL of methanol was added palladium on carbon (0.013 mg, 0.12 mmol). The mixture was placed under an atmosphere of hydrogen (1 atm) for 15 hours and was then filtered through a pad of Celite, which was washed with MeOH. The filtrate was concentrated in vacuo to provide the title compound that gave a proton NMR spectra consistent with theory and a mass ion (ES+) of 388.1657 for [M+H]$^+$ [Calculated for $C_{23}H_{22}N_3O_3$, [M+H]$^+$=388.1656].

Example 10

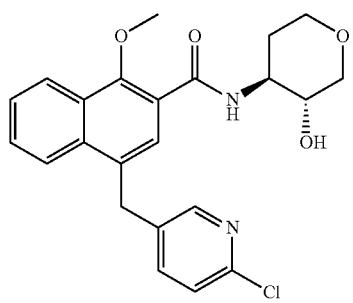 [SMILES: COc1c(C(=O)N[C@H]2CCOC[C@@H]2O)cc(Cc2ccc(Cl)nc2)c2ccccc12]

4-[(6-Chloropyridin-3-yl)methyl]-N-[(3R,4S)-3-hydroxytetrahydro-2H-pyran-4-yl]-1-methoxy-2-naphthamide

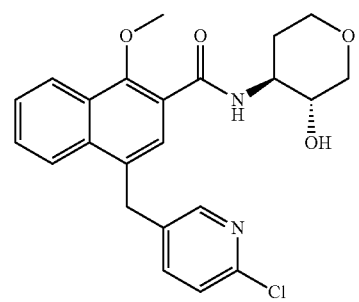

A. Synthesis of (3R,4S)-4-aminotetrahydro-2H-pyran-3-ol

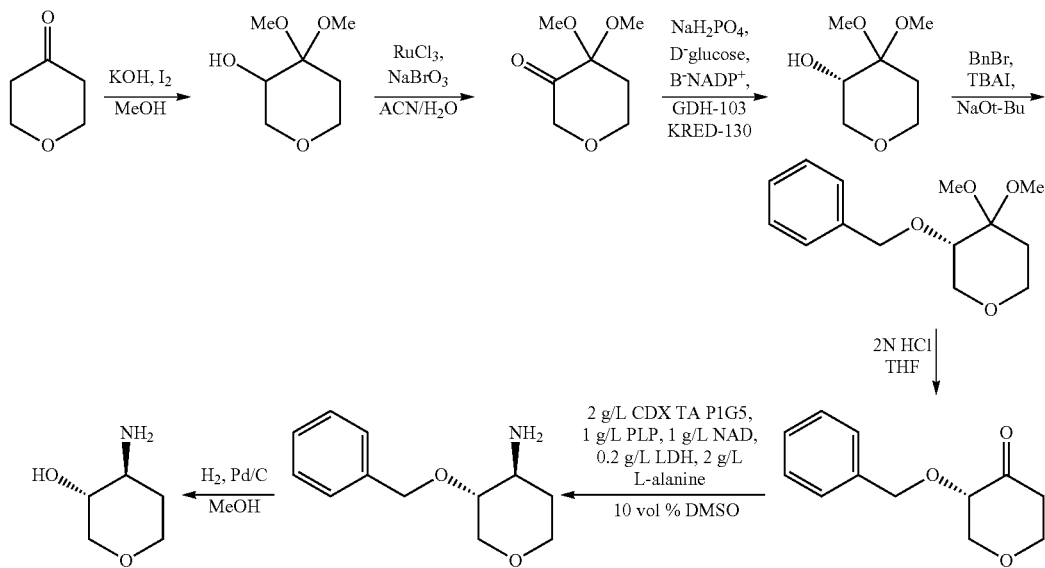

A jacketed flask equipped with an overhead stirrer and a thermocouple was charged with 23.0 L of MeOH, and cooled to 5° C. Potassium hydroxide (1.574 kg, 28.05 mol) was added to the flask, and the resulting solution was aged until homogeneous and recooled to 5° C. Tetrahydro-4H-pyran-4-one (1.00 kg, 10.0 mol) was then added at a steady rate over 20 minutes, and the resulting solution was aged for 20-30 minutes. A solution of iodine (2.778 kg, 10.95 mol) in 18.5 L of MeOH was then added via mechanical pump at a steady rate over 90-100 minutes. After an additional 30 minutes, the solution was warmed to room temperature and toluene (42.0 L) was added. The resulting slurry was concentrated in vacuo to a volume of about 8.4 L. Additional toluene (8.4 L) was added and the resulting solution was concentrated to a volume of 8.4 L 2×. The resulting slurry was then filtered, and the filter cake was rinsed 2× with toluene (4.0 L). The combined toluene streams were concentrated to about 6 L, and the product is extracted 2× with water (3.0 L) to provide 4,4-dimethoxytetrahydro-2H-pyran-3-ol.

To a solution of the above compound (1.00 kg, 6.17 mol) in 5 L of water was added acetic acid to pH 5.2-5.4. The mixture was diluted with acetonitrile (4.0 L) and ruthenium trichloride hydrate (6.4 g, 0.028 mol) was added and rinsed in with additional acetonitrile (1.0 L). The flask was placed in a room temperature water bath and a solution of sodium bromate (650 g, 4.31 mol) in water (1.95 L) was added slowly over approximately 30 minutes, keeping the temperature below 30° C. After 2 hours, potassium bicarbonate (430 g, 4.30 mol), sodium thiosulfate (1.07 kg, 4.31 mol), potassium chloride (500 g, 6.71 mol) and acetonitrile (5 L) were added sequentially. The layers were separated and the aqueous layer was extracted 3× with acetonitrile (10 L). The combined organic extracts were concentrated to about 4 L. Toluene (5 L) was then added and the mixture reconcentrated to 4 L 4×. The mixture was diluted with toluene (7 L) and filtered to remove solids. The filtercake was washed 3× with toluene (2 L) and the combined filtrate and washes were concentrated to a total volume of 3 L to provide an organic solution of 4,4-dimethoxydihydro-2H-pyran-3(4H)-one.

To a 3 L 3-neck RB flask with overhead stirring, thermocouple and heating mantle was added sodium dihydrogenphosphate (96.0 g, 800 mmol) in 1.6 L of water. Sodium hydroxide (29 mL, 50 wt %) was added to pH 7.13, followed by hydrochloric acid (5 mL, 6 N) to pH 7.02.

The above organic solution of 4,4-dimethoxydihydro-2H-pyran-3(4H)-one was extracted 3× with phosphate buffered water (0.55 L). To the combined aqueous extracts was added D-glucose (180 g, 100 mmol), and the solution was heated to 30° C. When the solution exceeded 27° C. upon heating B-NADP+ (1.60 g, 499 mmol), GDH-103 (1.60 g, 499 mmol), and KRED-130 (1.60 g, 499 mmol) were added and the mixture was stirred for 17 hours at 30° C. Potassium chloride (200 g, 2.68 mol) and acetonitrile (1.3 L) were added. After 30 minutes, the reaction mixture was transferred to 6 L separating funnel and additional MeCN (0.67 L) and toluene (0.87 L) were added. The aqueous layer was back extracted 1× with a mixture of acetonitrile (1.95 L) and toluene (0.65 L), and 1× with acetonitrile (1.5 L). The combined organic extracts were concentrated in vacuo to provide (3S)-4,4-dimethoxytetrahydro-2H-pyran-3-ol.

To a 2 L RB flask with overhead stirring, thermocouple, heating mantle and $N_2$ inlet was added a solution of the above compound (72.0 g, 0.444 mol) in 750 mL of THF. After 15 hours, sodium tert-butoxide (48.3 g, 492 mmol) was added in one portion, and the mixture was heated to 35° C. for 1 hour, and aged at 22° C. for 1 hour. Tetrabutylammonium iodide (8.19 g, 22.2 mmol) and benzyl bromide (56.5 ml, 466 mmol) were added, and the mixture was heated to 50° C. for 2 hours. The solution was cooled to 25° C., and water (750 mL) and MtBE (2.25 L) were added. The organic layer was separated from the aqueous and concentrated in vacuo. The resultant brown oil was purified via silica gel chromatography, eluting with 0-15% ethyl acetate in hexanes to provide (3S)-3-(benzyloxy)-4,4-dimethoxytetrahydro-2H-pyran.

To a solution of the above compound (61.1 g, 225 mmol) in 300 mL of THF was added 2 N HCl (300 mL, 0.600 mol). After 1.5 hours, saturated aqueous potassium carbonate (60 mL) was added via addition funnel to pH 7.4. The aqueous layer was extracted 3× with MtBE (300 mL) and the combined organic extracts were concentrated in vacuo to provide crude (3S)-3-(benzyloxy)tetrahydro-4H-pyran-4-one.

To a solution of L-Alanine (200 g, 2.24 mol), sodium formate (76.0 g, 1.12 mmol), and sodium phosphate dibasic (28.7 g, 202 mmol) in 2.25 L of water adjusted to pH 7.5 was added NAD (2.2 g, 3.21 mmol), pyridoxal-5-phosphate (2.2 g, 8.90 mmol), LDH (0.45 g, 0.22 mol), FDH (4.5 g, 0.20 mol), and TA P1G5 (4.5 g, 0.22 mol). After all the components were completely dissolved, (3S)-3-(benzyloxy)tetrahydro-4H-pyran-4-one (45 g, 0.22 mol) was added and the pH was adjusted to pH 7.25 with 6 N HCl and aged at 30° C. After 15 hours, potassium carbonate (700 g, 5.06 mol) was added slowly, followed by ethyl acetate (2.2 L). The mixture was filtered through a bed of Solka Floc and the cake was washed with ethyl acetate (250 mL). The combined filtrates were separated and the aqueous layer was extracted a second time with ethyl acetate (2 L). The combined organic extracts were concentrated in vacuo to provide crude (3R,4S)-3-(benzyloxy)tetrahydro-2H-pyran-4-amine.

To a solution of the above compound (38.8 g, 0.187 mol) in 730 mL of methanol was added concentrated hydrochloric acid (23.3 mL). The solution was subjected to hydrogenation at 40 psi $H_2$, 25° C. over 5.8 g of 10% Pd/C (5.8 g). After 15 hours, the mixture was filtered through solka floe and the filtercake was washed 5× with methanol (100 mL). The combined filtrate and washes were concentrated in vacuo to provide (3R,4S)-4-aminotetrahydro-2H-pyran-3-ol that gave proton NMR spectra consistent with theory.

B. Synthesis of 4-[(6-Chloropyridin-3-yl)methyl]-N-[(3R,4S)-3-hydroxytetrahydro-2H-pyran-4-yl]-1-methoxy-2-naphthamide The title compound was prepared by the procedure described for the synthesis of 4-[(6-chloropyridin-3-yl)methyl]-N-[(1S,2S)-2-hydroxycyclohexyl]-1-methoxy-2-naphthamide in Example 3, substituting (3R,4S)-4-aminotetrahydro-2H-pyran-3-ol for (1S,2S)-2-aminocyclohexanol. The resultant solid gave a proton NMR spectra consistent with theory and a mass ion (ES+) of 426.9 for [M+H]$^+$: $^1$H NMR (400 MHz, CDCl$_3$) δ 8.31 (s, 1H), 8.24-8.19 (m, 2H), 7.99 (s, 1H), 7.87-7.84 (m, 1H), 7.62-7.55 (m, 2H), 7.39-7.36 (m, 1H), 7.17 (d, J=8.2 Hz, 1H), 4.38 (s, 2H), 4.15-4.10 (m, 2H), 4.09-4.00 (m, 1H), 4.03 (s, 3H), 3.70-3.63 (m, 1H), 3.54-3.47 (m, 1H), 3.28-3.23 (m, 1H), 2.12-2.04 (m, 1H), 1.84-1.74 (m, 1H).

Example 11

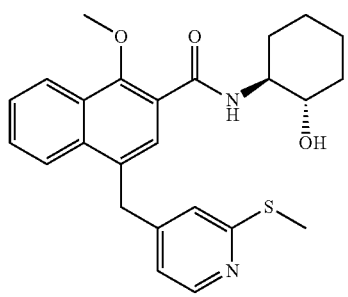 [SMILES: COc1c(C(=O)N[C@H]2CCCC[C@@H]2O)cc(Cc2ccnc(SC)c2)c2ccccc12]

N-[(1S,2S)-2-Hydroxycyclohexyl]-1-methoxy-4-{[2-(methylthio)pyridin-4-yl]methyl}-2-naphthamide

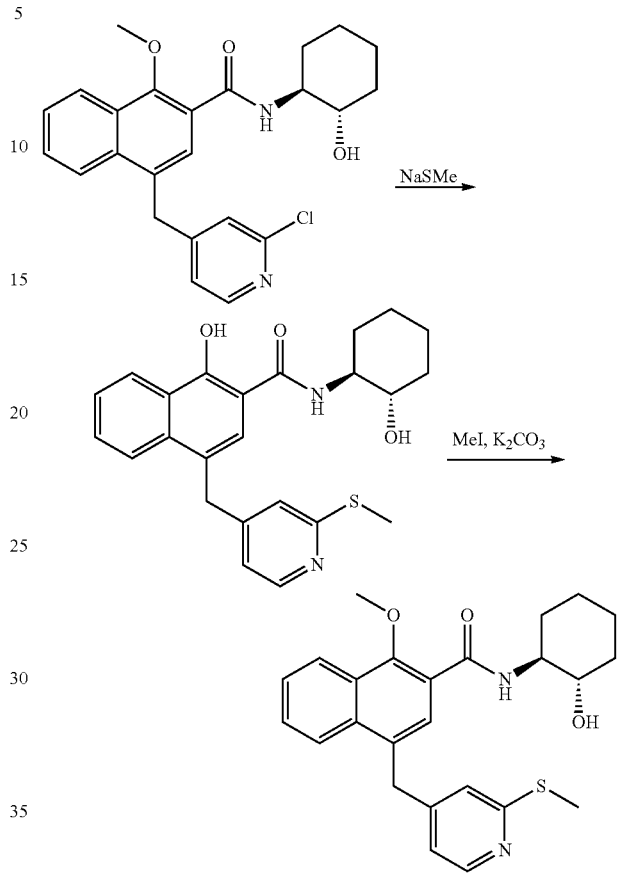

4-Bromo-N-[(1S,2S)-2-hydroxycyclohexyl]-1-methoxy-2-naphthamide was prepared by the procedure described for the synthesis of 4-formyl-N-[(1S,2S)-2-hydroxycyclohexyl]-1-methoxy-2-naphthamide in Example 8, substituting 4-bromo-1-methoxy-2-naphthoate (see Example 2) for methyl 4-formyl-1-methoxy-2-naphthoate.

4-[(2-Chloropyridin-4-yl)methyl]-N-[(1S,2S)-2-hydroxycyclohexyl]-1-methoxy-2-naphthamide was prepared by the procedure described for the synthesis of 1-methoxy-4-[4-(1H-pyrazol-1-yl)benzyl]-2-naphthoic acid in Example 2, substituting 4-(bromomethyl)-2-chloropyridine for 1-[4-(bromomethyl)phenyl]-1H-pyrazole, and substituting 4-bromo-N-[(1S,2S)-2-hydroxycyclohexyl]-1-methoxy-2-naphthamide for methyl 4-bromo-1-methoxy-2-naphthoate.

To a solution of 4-[(2-chloropyridin-4-yl)methyl]-N-[(1S,2S)-2-hydroxycyclohexyl]-1-methoxy-2-naphthamide (0.050 g, 0.12 mmol) in 1 mL of DMSO was added sodium thiomethoxide (0.025 g, 0.35 mmol). The mixture was heated in a sealed tube at 100° C. for 18 hours, then cooled to room temperature. Additional sodium thiomethoxide (0.025 g, 0.35 mmol) was added, and the reaction was heated to 120° C. for 3 hours, then recooled to room temperature and diluted with ethyl acetate and water. The aqueous layer was extracted 3× with ethyl acetate and the combined organic fractions were washed with brine, dried over sodium sulfate, filtered, and concentrated in vacuo to provide 1-hydroxy-N-[(1S,2S)-2-hydroxycyclohexyl]-4-{[2-(methylthio)pyridin-4-yl]methyl}-2-naphthamide that gave a mass ion (ES+) of 423.0 for [M+H]$^+$.

To a solution of the above compound (0.050 g, 0.12 mmol) in 5 mL of DMF was added potassium carbonate (0.033 g, 0.24 mmol) and iodomethane (0.018 g, 0.13 mmol). After 5 hours, the reaction was diluted with water and extracted 3× with ethyl acetate. The combined organic fractions were washed with brine, dried over sodium sulfate, filtered, and concentrated in vacuo. The residue was purified via silica gel chromatography, eluting with 10-60% ethyl acetate in hexanes to provide the title compound that gave a proton NMR spectra consistent with theory and a mass ion (ES+) of 437.2 for [M+H]+: $^1$H NMR (400 MHz, CDCl$_3$) δ 8.28 (d, J=5.1 Hz, 1H), 8.21 (d, J=8.4 Hz, 1H), 8.09 (d, J=7.1 Hz, 1H), 8.01 (s, 1H), 7.81 (d, J=7.7 Hz, 1H), 7.60-7.52 (m, 2H), 6.98 (s, 1H), 6.78 (d, J=5.1 Hz, 1H), 4.33 (s, 2H), 4.03 (s, 3H), 3.98-3.93 (m, 1H), 3.57-3.49 (m, 2H), 2.51 (s, 3H), 2.15-2.13 (m, 2H), 1.82-1.78 (m, 2H), 1.50-1.36 (m, 3H).

Example 12

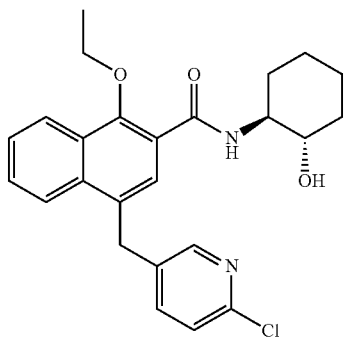 [SMILES: CCOc1c(C(=O)N[C@H]2CCCC[C@@H]2O)cc(Cc2ccc(Cl)nc2)c2ccccc12]

4-[(6-Chloropyridin-3-yl)methyl]-1-ethoxy-N-(1S, 2S)-2-hydroxycyclohexyl)-2-naphthamide

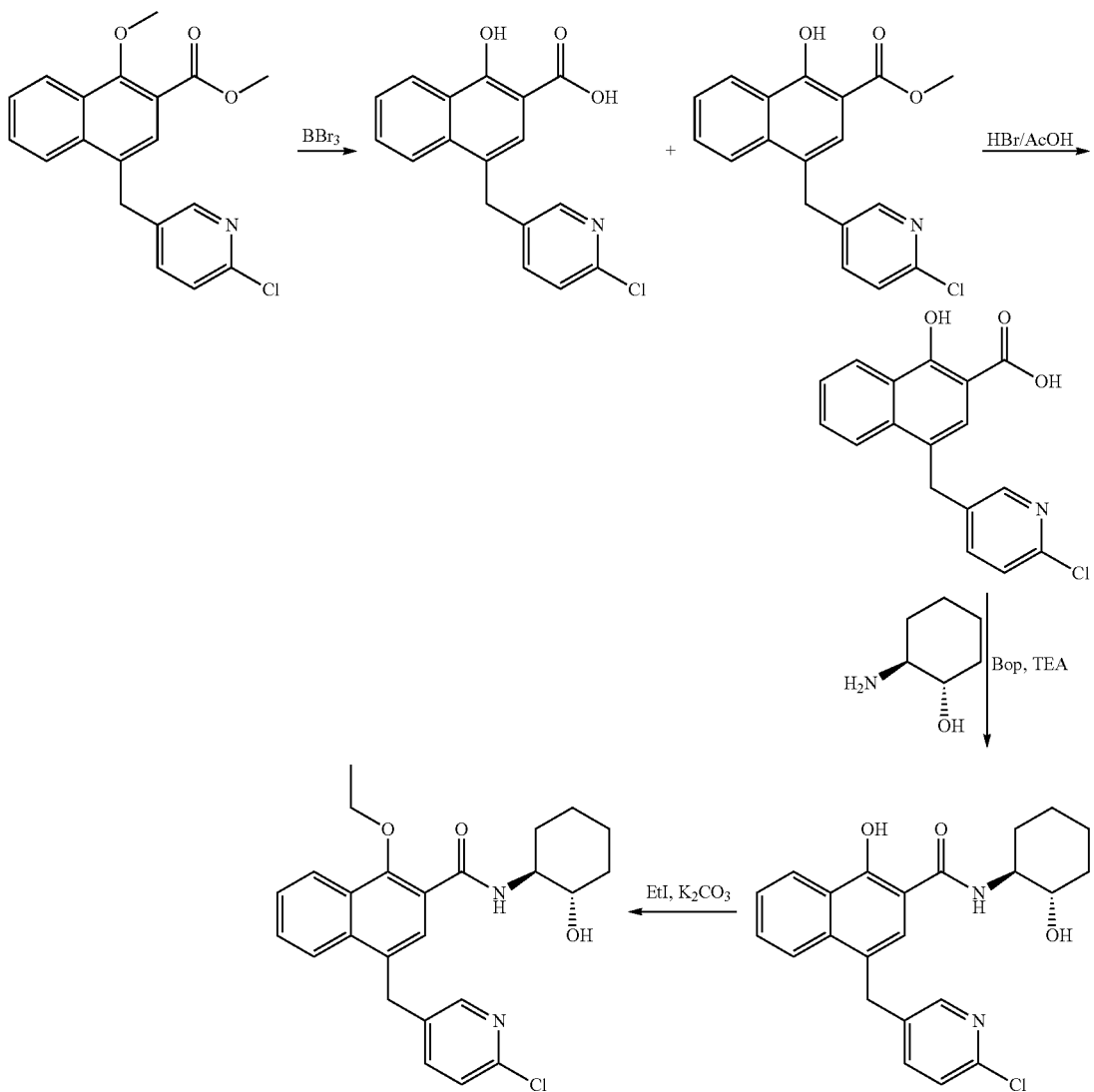

To a solution of methyl 4-[(6-chloropyridin-3-yl)methyl]-1-methoxy-2-naphthoate (see Example 3, 0.200 g, 0.585 mmol) in 5 mL of dichloromethane at −78° C. was added boron tribromide (1.0 M in dichloromethane, 1.76 mL, 1.76 mmol) dropwise. After 1 hour, the reaction was warmed to 0° C., treated with 6 mL of MeOH and warmed to room temperature overnight. To this reaction was added hydrobromic acid (33% in acetic acid, 2.50 mL, 15.2 mmol) dropwise, and the mixture was heated to 65° C. for 60 hours. Addition hydrobromic acid (33% in acetic acid, 1.50 mL, 9.14 mmol) was added, and the reaction was heated to 90° C. for 4 hours, cooled to room temperature, azeotroped 2× with toluene, and concentrated in vacuo to provide 4-[(6-chloropyridin-3-yl)methyl]-1-hydroxy-2-naphthoic acid that gave a mass ion (ES+) of 314.2 for $[M+H]^+$.

To a solution of the above compound (0.600 g, 1.91 mmol) in 5 mL of DMF was added (1H-1,2,3-benzotriazol-1-yloxy)[tris(dimethylamino)]phosphonium hexafluorophosphate (1.69 g, 3.82 mmol), (1S,2S)-2-aminocyclohexanol (0.330 g, 2.87 mmol), and triethylamine (0.67 mL, 4.8 mmol). After 2 hours, the reaction was diluted with ethyl acetate, washed with water and brine, dried over sodium sulfate, filtered, and concentrated in vacuo. The residue was purified via silica gel chromatography, eluting with 20-40% ethyl acetate in hexanes to provide 4-[(6-chloropyridin-3-yl)methyl]-1-hydroxy-N-[(1S,2S)-2-hydroxycyclohexyl]-2-naphthamide that gave a proton NMR spectra consistent with theory and a mass ion (ES+) of 41.3 for $[M+H]^+$.

To a solution of the above compound (0.060 g, 0.15 mmol) in 1 mL of DMF was added potassium carbonate (0.022 g, 0.16 mmol) and iodoethane (0.025 g, 0.16 mmol). After 4 hours, the reaction was diluted with water and extracted 3× with ethyl acetate. The combined organic fractions were washed with brine, dried over sodium sulfate, filtered, and concentrated in vacuo. The residue was purified via silica gel chromatography, eluting with 40-60% ethyl acetate in hexanes to provide the title compound that gave a proton NMR spectra consistent with theory and a mass ion (ES+) of 439.4 for $[M+H]^+$: $^1$H NMR (400 MHz, $CDCl_3$) δ 8.32 (d, J=2.4 Hz, 1H), 8.20-8.16 (m, 2H), 7.99 (s, 1H), 7.86-7.81 (m, 1H), 7.59-7.52 (m, 2H), 7.39-7.36 (m, 1H), 7.16 (d, J=8.2 Hz, 1H), 4.37 (s, 2H), 4.22-4.10 (m, 2H), 4.03-3.92 (m, 1H), 3.70 (br s, 1H), 3.49 (br s, 1H), 2.17-2.04 (m, 2H), 1.82-1.75 (m, 2H), 1.56 (t, J=7.1 Hz, 3H), 1.50-1.27 (m, 4H).

Example 13

A. Biological Activity

The utility of the compounds as M1 receptor positive allosteric modulators may be demonstrated by methodology known in the art including by the assay described below. The assay is designed to select compounds that possess modulator activity at the acetylcholine muscarinic M1 receptor or other muscarinic receptors expressed in CHOnfat cells by measuring the intracellular calcium with a FLIPR$^{384}$ Fluorometric Imaging Plate Reader System. The assay studies the effect of one or several concentrations of test compounds on basal or acetylcholine-stimulated $Ca^{2+}$ levels using FLIPR.

For each compounds of the invention that was evaluated, the compound is prepared and subjected to a pre-incubation period of four minutes. Thereafter, a single $EC_{20}$ concentration of acetylcholine is added to each well (3 nM final). The intracellular $Ca^{2+}$ level of each sample is measured and compared to an acetylcholine control to determine any modulatory activity.

Cells: CHOnfat/hM1, hM2, hM3 or hM4 cells are plated 24 hours before the assay at a density of 18,000 cells/well (100 μL) in a 384 well plate. CHOnfat/hM1 and CHOnfat/hM3 Growth Medium: 90% DMEM (Hi Glucose); 10% HI FBS; 2 mM L-glutamine; 0.1 mM NEAA; Pen-Strep; and 1 mg/ml Geneticin, are added. For M2Gqi5CHOnfat and M4Gqi5CHOnfat cells, an additional 600 μg/ml hygromycin is added.

Equipment: 384 well plate, 120 μL addition plate; 96-well Whatman 2 ml Uniplate Incubator, 37° C., 5% $CO_2$; Skatron EMBLA-384 Plate Washer; Multimek Pipetting System; Genesis Freedom 200 System; Mosquito System; Temo Nanoliter Pipetting System; and FLIPR$^{384}$ Fluorometric Imaging Plate Reader System are used.

Buffers: Assay Buffer: Hanks Balanced Salt Solution, with 20 mM Hepes, 2.5 mM Probenecid (Sigma P-8761) first dissolved in 1 N NaOH, 1% Bovine Serum Albumin (Sigma A-9647). Dye Loading Buffer: Assay Buffer plus 1% Fetal Bovine Serum and Fluo-4AM/Pluronic Acid Mixture. 2 mM Fluo-4AM ester stock in DMSO (Molecular Probes F-14202) Concentration of 2 μM in buffer for a final concentration of 1 μM in Assay. 20% Pluronic acid solution stock, with a concentration of 0.04% in Buffer, 0.02% in Assay. 65 μL of 2 mM Fluo-4AM are mixed with 130 μL of 20% pluronic acid. The resulting solution and 650 μL FBS is added to the assay buffer for a total volume of 65 mL.

Positive Controls: 4-Br-A23187: 10 mM in DMSO, final concentration 10 μM. Acetylcholine: 10 μM in water, working stock at both 20 μM and 30 μM in assay buffer, final concentration of 10 μM. This is used to check the maximum stimulation of the CHOK1/hM1 cells. 20 μM (2×) acetylcholine is added in the preincubation part of the assay, and the 30 μM (3×) stock is added in the second part. ($EC_{20}$)Acetylcholine: 10 mM in water, working stock of 9 nM (3×), and final concentration in assay is 3 nM. This is used after the preincubation with test compounds. Addition of the $EC_{20}$ Acetylcholine to each well with a test compound will ascertain any modulator activity. 24 wells contain 3 nM Acetylcholine alone as a control.

B. Determining Activity of Putative Compounds

Screening Plate Compounds are titrated in 96-well plates (columns 2-11), 100% DMSO, started at a concentration of 15 mM (150× stock concentration), and 3-fold serial dilutions using Genesis Freedom200 System. Four 96-well plates are combined into a 384-well plate using Mosquito Nanoliter Pipetting System by transferring 1 μl of serial diluted compounds to each well, and 1 mM acetylcholine (100× stock concentration) were added as a control. Using Temo, 49 μl assay buffer is added to each well of the 384-well plate right before assay.

In a 96-well Whatman 2 ml Uniplate, 9 nM Acetylcholine (3×) is pipetted into wells corresponding to the screening compounds, and into control wells. The 30 μM acetylcholine control (3×) is added into control wells, and the 3× agonist plate is transferred into a 384 well plate.

Cells are washed three times with 100 μL of buffer, leaving 30 μL of buffer in each well. Using Multimek, 30 μL of Dye Loading Buffer is added into each well and incubated at 37° C., 5% $CO_2$ for up to one hour.

After 60 minutes, the cells are washed three times with 100 μL of buffer, leaving 30 μL of buffer in each well. The cell plate, screening plate, and agonist addition plates are placed on the platform in the FLIPR and the door closed. A signal test to check background fluorescence and basal fluorescence signal is performed. Laser intensity is adjusted if necessary.

Four minutes of pre-incubation with the test compounds is provided to determine any agonist activity on the M1 receptor by comparison to the 1 mM acetylcholine control. After pre-incubation, the $EC_{20}$ value of acetylcholine (3 nM final) is added to determine any modulator activity.

A further description of the muscarinic FLIPR assay can be found in Conn et al., PCT/US2004/004735, which published as WO 2004/073639. The inflection print values (IP Values) from the FLIPR assay for the compounds of the invention are shown in Tables 1 and 2.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. Compound of formula (I):

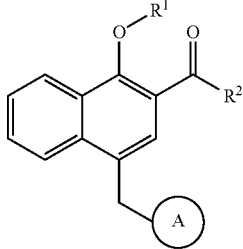

wherein
$R^1$ is selected from the group consisting of
 (1) hydrogen,
 (2) —$R^3$,
 (3) —$C_{1-6}$ alkyl,
 (4) —$C_{2-6}$ alkenyl, and
 (5) —$C(O)N(R^4)_2$,
 wherein each is optionally substituted with one or more $R^a$;
$R^2$ is selected from the group consisting of
 (1) hydroxyl, and
 (2) —$N(R^4)_2$,
 wherein each is optionally substituted with one or more $R^a$;
$R^3$ and $R^4$ are independently selected from the group consisting of
 (1) hydrogen,
 (2) hydroxyl,
 (3) —$C_{1-6}$ alkyl,
 (4) —$C_{3-10}$ cycloalkyl, and
 (5) —$C_{5-10}$ heterocyclyl,
 wherein each is optionally substituted with one or more $R^a$;
A is selected from the group consisting of
 (1) —$C_{6-10}$ aryl, and
 (2) —$C_{6-10}$ heteroaryl,
 wherein each is optionally substituted with one or more $R^a$;
$R^a$ is selected from the group consisting of
 (1) hydrogen,
 (2) hydroxyl,
 (3) halogen,
 (4) —O,
 (5) —$C_{1-6}$ alkyl,
 (6) —$C_{3-10}$ cycloalkyl, which is unsubstituted or substituted with one or more hydroxyl,
 (7) —$C_{5-10}$ heteroaryl, which is unsubstituted or substituted with one or more hydroxyl,
 (8) —CN,
 (9) —$OR^3$,
 (10) —$SR^3$,
 (11) —$N(R_4)_n$, and
 (12) —$C(O)R^3O(C)O$;
n is independently 1 to 4;
or a pharmaceutically acceptable salt thereof, provided $R^1$ is not hydrogen when A is phenyl and $R^2$ is hydroxyl.

2. A compound of claim 1, or a pharmaceutically acceptable salt thereof, wherein $R^1$ is selected from the group consisting of
 (1) hydrogen,
 (2) methyl,
 (3) ethyl,
 (4) ethylenyl, and
 (5) $C(O)NHCH_2CH_3$.

3. A compound of claim 1, or a pharmaceutically acceptable salt thereof, wherein $R^2$ is $N(R^4)_2$ and each $R^4$ is independently selected from the group consisting of
 (1) hydrogen,
 (2) —$C_{3-10}$ cycloalkyl, and
 (3) —$C_{5-10}$ heterocyclyl,
wherein said cycloalkyl and said heterocyclyl are optionally substituted with one or more $R^a$.

4. A compound of claim 1, or a pharmaceutically acceptable salt thereof, wherein A is selected from the group consisting of
 (1) phenyl,
 (2) pyridyl,
 (3) piperazinyl,
 (4) biphenyl, and
 (5) bipyridyl
wherein said cycloalkyl and said heterocyclic are optionally substituted with one or more $R^a$.

5. A compound of claim 1 or a pharmaceutically acceptable salt thereof, wherein $R^1$ is hydrogen.

6. A compound of claim 1 or a pharmaceutically acceptable salt thereof, wherein $R^1$ is methyl.

7. A compound of claim 1 or a pharmaceutically acceptable salt thereof, where $R^2$ is hydroxyl.

8. A compound of claim 1 or a pharmaceutically acceptable salt thereof, where $R^2$ is $N(R^4)_2$ and $R^4$ is hydrogen and $C_{3-10}$ cycloalkyl, which is optionally substituted with one or more $R^a$.

9. A compound of claim 1 or a pharmaceutically acceptable salt thereof, where $R^2$ is $N(R^4)_2$ and $R^4$ is hydrogen and cyclohexyl, which is optionally substituted with one or more $R^a$.

10. A compound of claim 1 or a pharmaceutically acceptable salt thereof, where $R^2$ is $N(R^4)_2$ and $R^4$ is hydrogen and cyclohexyl, which is optionally substituted with one or more hydroxyl.

11. A compound of claim 1 or a pharmaceutically acceptable salt thereof, wherein $R^3$ is —$C_{1-6}$ alkyl.

12. A compound of claim 1, which is selected from the group consisting of
1-Methoxy-4-(4-methoxybenzyl)-2-naphthoic acid;
1-Methoxy-4-[4-(1H-pyrazol-1-yl)benzyl]-2-naphthoic acid;
4-[(6-Chloropyridin-3-yl)methyl]-N-[(1S,2S)-2-hydroxy-cyclohexyl]-1-methoxy-2-naphthamide;

N-[(1S,2S)-2-Hydroxycyclohexyl]-1-methoxy-4-[(6-methylpyridin-3-yl)methyl-2-naphthamide;

N-[(1S,2S)-2-Hydroxycyclohexyl]-1-methoxy-4-{[6-(1-methyl-1H-pyrazol-4-yl)pyridine-3-yl]methyl}-2-naphthamide;

1-Hydroxy-N-[(1S,2S)-2-hydroxycyclohexyl]-4-{[6-(1H-pyrazol-1-yl)pyridine-3-yl]methyl}-2-naphthamide;

N-[(1S,2S)-2-Hydroxycyclohexyl]-1-methoxy-4-{[6-(1H-pyrazol-1-yl)pyridine-3-yl]methyl}-2-naphthamide;

N-[(1S,2S)-2-Hydroxycyclohexyl]-1-methoxy-4-{[4-(1-methyl-1H-pyrazol-4-yl)piperazin-1-yl]methyl}-2-naphthamide;

N-[(1S,2S)-2-Hydroxycyclohexyl]-1-methoxy-4-[(6-vinylpyridin-3-yl)methyl]-2-naphthamide;

4-[(6-Chloropyridin-3-yl)methyl]-N-[(3R,4S)-3-hydroxytetrahydro-2H-pyran-4-yl]-1-methoxy-2-naphthamide;

N-[(1S,2S)-2-Hydroxycyclohexyl]-1-methoxy-4-{[2-(methylthio)pyridin-4-yl]methyl}-2-naphthamide; and 4-[(6-Chloropyridin-3-yl)methyl]-1-ethoxy-N-(1S,2S)-2-hydroxycyclohexyl]-2-naphthamide or a pharmaceutically acceptable salt thereof.

13. A compound of claim 1 represented by structural formula (II):

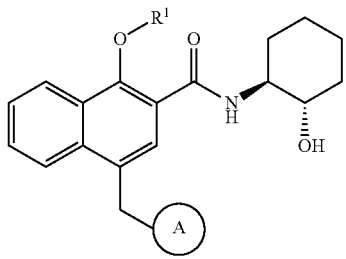

or a pharmaceutically acceptable salt thereof, wherein $R^1$ and A are as defined in claim 1.

14. A compound of claim 13, or a pharmaceutically acceptable salt thereof, wherein $R^1$ is selected from the group consisting of
(1) hydrogen,
(2) methyl,
(3) ethyl,
(4) —$C_{2-6}$ alkenyl, and
(5) —$C(O)N(R^4)_2$,
wherein each is optionally substituted with one or more $R^a$.

15. A compound of claim 14, or a pharmaceutically acceptable salt thereof, wherein A is selected from the group consisting of
(1) phenyl,
(2) pyridyl,
(3) piperazinyl,
(4) biphenyl, and
(5) bipyridyl.

16. A compound of claim 14, or a pharmaceutically acceptable salt thereof, wherein A is

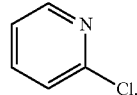

17. A pharmaceutical composition comprising a therapeutically effective amount of a compound of claim 1, or a pharmaceutically acceptable salt thereof, and a pharmaceutically acceptable carrier.

18. A method of treating a disease or disorder mediated by the muscarinic M1 receptor, wherein said disease or disorder is selected from the group consisting of Alzheimer's disease, schizophrenia, pain and sleep disorders in a patient in need thereof, comprising administering to the patient a therapeutically effective amount of a compound of claim 1 or a pharmaceutically acceptable salt thereof, and a pharmaceutically acceptable carrier.

* * * * *